United States Patent
Parker et al.

(10) Patent No.: US 10,533,955 B2
(45) Date of Patent: Jan. 14, 2020

(54) METHOD AND APPARATUS FOR MEASURING A COMPOSITION OF A MULTIPHASE FLUID

(71) Applicant: M-Flow Technologies Limited, Abingdon (GB)

(72) Inventors: Alan Parker, Abingdon (GB); Giles Edward, Abingdon (GB); Arnault Tremolet, Abingdon (GB); Alex Wall-Clarke, Abingdon (GB)

(73) Assignee: M-Flow Technologies Ltd, Abingdon (GB)

( * ) Notice: Subject to any disclaimer, the term of this patent is extended or adjusted under 35 U.S.C. 154(b) by 312 days.

(21) Appl. No.: 15/553,560

(22) PCT Filed: Feb. 26, 2016

(86) PCT No.: PCT/GB2016/050507
§ 371 (c)(1),
(2) Date: Aug. 24, 2017

(87) PCT Pub. No.: WO2016/135506
PCT Pub. Date: Sep. 1, 2016

(65) Prior Publication Data
US 2018/0045659 A1    Feb. 15, 2018

(30) Foreign Application Priority Data
Feb. 27, 2015    (GB) .................................. 1503348.3

(51) Int. Cl.
*G01N 22/00*    (2006.01)
*G01N 9/24*    (2006.01)
(Continued)

(52) U.S. Cl.
CPC ............... *G01N 22/00* (2013.01); *G01N 9/24* (2013.01); *G01N 23/12* (2013.01); *G01N 33/2823* (2013.01); *G01N 2223/635* (2013.01)

(58) Field of Classification Search
CPC .......... G01N 22/00; G01N 9/24; G01N 23/12; G01N 33/2823; G01N 27/221; G01N 2223/635
(Continued)

(56) References Cited

U.S. PATENT DOCUMENTS 4,352,288 A * 10/1982 Paap ..................... G01R 27/22
378/54
5,049,823 A    9/1991 Castel et al.
(Continued)

FOREIGN PATENT DOCUMENTS

| GB | 2511045 | 8/2014 |
| WO | WO 93/21501 | 10/1993 |
| WO | WO 2014/064436 | 5/2014 |

OTHER PUBLICATIONS

Arvoh, Benjamin Kaku et al., "Estimation of volume fraction and flow regime identification in inclined pipes based on gamma measurements and multivariate calbration," J. Chemometrics, vol. 26, Issue 8-9, pp. 425-434 (Aug.-Sep. 2012).
(Continued)

*Primary Examiner* — Marrit Eyassu
(74) *Attorney, Agent, or Firm* — Levy & Grandinetti

(57) ABSTRACT

A method for use in measuring a composition of a multiphase fluid which includes flowing a multiphase fluid through a fluid flow path defined by a wall of a fluid conduit is disclosed. The wall includes an electrically non-conductive material. The method includes establishing an electromagnetic field which extends through the electrically non-conductive material of the wall of the fluid conduit into the fluid and measuring a property of the electromagnetic field
(Continued)

over a measurement time period. The method also includes transmitting additional energy through the fluid over the measurement time period independently of the electromagnetic field and measuring the additional energy transmitted through the fluid over the measurement time period. The method may be used to unambiguously determine a composition of a multiphase fluid which has different components.

63 Claims, 8 Drawing Sheets

(51) Int. Cl.
  G01N 23/12 (2018.01)
  G01N 33/28 (2006.01)
(58) Field of Classification Search
  USPC ...................................................... 73/861.11
  See application file for complete search history.

(56) References Cited

U.S. PATENT DOCUMENTS

| | | | | |
|---|---|---|---|---|
| 5,259,239 | A * | 11/1993 | Gaisford | G01F 1/74 |
| | | | | 73/61.44 |
| 7,775,085 | B2 * | 8/2010 | Scott | G01N 33/2847 |
| | | | | 73/61.43 |
| 8,061,186 | B2 * | 11/2011 | Gysling | G01N 29/024 |
| | | | | 73/61.54 |
| 9,719,821 | B2 * | 8/2017 | Liao | A01J 5/01 |
| 2008/0319685 | A1 | 12/2008 | Xie et al. | |
| 2012/0087467 | A1 | 4/2012 | Tjugum | |

OTHER PUBLICATIONS

Eberle, C.S. et al., "Optimization of a one-shot gamma densitometer for measuring area-averaged void fractions of gas-liquid flows in narrow pipelines," Measurement Science and Technology, vol. 5, No. 9, pp. 1146-1158 (Sep. 1, 1994).

\* cited by examiner

METHOD AND APPARATUS FOR MEASURING A COMPOSITION OF A MULTIPHASE FLUID

FIELD

The methods and apparatus described herein relate to measuring a composition of a fluid and, in particular, though not exclusively, to measuring a composition of a multiphase fluid comprising different components such as oil, water and gas.

BACKGROUND

As used herein, the term "gas void fraction" (GVF) of a fluid may be defined as the ratio of the volume of gas present in the fluid to the total volume of the fluid.

Also, as used herein, the term "water-cut" of a fluid may be defined as the ratio of the volume of water present in the fluid to the volume of total liquids present in the fluid.

Fluids produced from oil and gas wells may be multiphase fluids having two or three different components. In particular, it is not uncommon for fluids produced from an oil or gas well to include oil, water and gas. The water-cut of a fluid produced from an oil or gas well can be a valuable piece of information because the economic value of the produced fluid is largely determined by the relative proportions of oil and water regardless of the relative proportion of any gas present.

It is known to use a gamma-ray beam for measuring the density of a multiphase fluid flowing through a steel pipe. In such a known system, one or more gamma-ray beams may be transmitted across one or more corresponding chordal paths such as one or more diametric paths across the fluid flow path defined by the pipe. The use of one or more such gamma-ray beams may result in a measured density of the fluid which is sensitive to changes in the flow regime of the fluid within the fluid flow path.

SUMMARY

It should be understood that any one or more of the features of one of the methods or apparatus described herein may be used alone or in any combination with any one or more of the features of the other methods or apparatus described herein.

A method is described herein for use in measuring a composition of a multiphase fluid.

The method may comprise flowing a multiphase fluid through a fluid flow path defined by a wall of a fluid conduit.

The wall may comprise an electrically non-conductive material.

The method may comprise establishing an electromagnetic field which extends through the electrically non-conductive material of the wall of the fluid conduit into the fluid.

The method may comprise measuring a property of the electromagnetic field over a measurement time period so as to provide a measured temporal variation in the property of the electromagnetic field.

The method may comprise transmitting additional energy through the fluid over the measurement time period independently of the electromagnetic field.

The method may comprise measuring the additional energy transmitted through the fluid over the measurement time period.

The method may comprise:
flowing a multiphase fluid through a fluid flow path defined by a wall of a fluid conduit, the wall comprising an electrically non-conductive material;
establishing an electromagnetic field which extends through the electrically non-conductive material of the wall of the fluid conduit into the fluid;
measuring a property of the electromagnetic field over a measurement time period so as to provide a measured temporal variation in the property of the electromagnetic field;
transmitting additional energy through the fluid over the measurement time period independently of the electromagnetic field; and
measuring the additional energy transmitted through the fluid over the measurement time period.

Such a method may be used to unambiguously determine a composition of a multiphase fluid which has different components. The method may, in particular, be used to unambiguously determine a water-cut value for a multiphase fluid comprising three components such as oil, water and gas.

The method may comprise establishing the electromagnetic field across the fluid flow path.

Establishing an electromagnetic field which extends through the wall of the fluid conduit across the fluid flow path may provide a relatively uniform electromagnetic field across the fluid flow path. This may help to reduce the sensitivity of a measurement of the property of the electromagnetic field to the distribution of any different fluid components across the fluid flow path. For example, this may help to reduce the sensitivity of a measurement of the resonant frequency of the electromagnetic field to the distribution of any different fluid components across the fluid flow path.

Use of an electrically non-conductive material in the wall of the fluid conduit may allow a stronger electromagnetic field to be established in the fluid compared with use of an electrically conductive material in the wall of the fluid conduit. Use of an electrically non-conductive material in the wall of the fluid conduit may therefore enhance the sensitivity of the measurement of the property of the electromagnetic field compared with use of an electrically conductive material in the wall of the fluid conduit.

The electrically non-conductive material of the wall may define at least part of a thickness of the wall of the fluid conduit.

The method may comprise selecting the configuration of the wall to enhance the uniformity of the electromagnetic field across the fluid flow path. The method may comprise selecting the material and/or thickness of the wall to enhance the uniformity of the electromagnetic field across the fluid flow path.

The electromagnetic field may comprise a radio frequency (RF) electromagnetic field.

The method may comprise confining the electromagnetic field in a cavity such as a resonant cavity through which the fluid flow path extends. The cavity may include the electrically non-conductive material of the wall of the fluid conduit.

The property of the electromagnetic field may comprise a resonant frequency of the electromagnetic field.

The additional energy transmitted through the fluid may comprise electromagnetic energy of a different frequency to the electromagnetic field.

The additional energy transmitted through the fluid may comprise gamma radiation and/or gamma-rays.

The additional energy transmitted through the fluid may comprise X-ray radiation and/or X-rays.

The additional energy transmitted through the fluid may be of a different type to any energy coupled between the electromagnetic field and the fluid.

The additional energy transmitted through the fluid may comprise acoustic energy.

The method may comprise transmitting the additional energy through the electrically non-conductive material of the wall of the fluid conduit in addition to transmitting the additional energy through the fluid. The method may comprise measuring the additional energy transmitted through the fluid and the electrically non-conductive material of the wall of the fluid conduit over the measurement time period.

Transmitting the additional energy through the electrically non-conductive material of the wall of the fluid conduit may permit a transmitter and/or receiver of the additional energy to be located externally of the wall of the fluid conduit or to be at least partially embedded and/or to be at least partially enclosed within the wall of the fluid conduit so that the transmitter and/or receiver do not protrude or extend into the fluid flow path. Transmitting the additional energy through the electrically non-conductive material of the wall of the fluid conduit may avoid any requirement to form or define an aperture which extends through the wall of the fluid conduit. Consequently, the wall may have improved strength and/or pressure integrity.

Transmitting the additional energy through the electrically non-conductive material of the wall of the fluid conduit may serve to reduce the measurement time period required to measure the additional energy transmitted through the fluid for a source of the additional energy of a given power or signal strength and for a given signal-to-noise ratio (SNR) compared with transmitting the additional energy through an electrically conductive material. Conversely, transmitting the additional energy through the electrically non-conductive material of the wall of the fluid conduit may increase the SNR achieved for a source of the additional energy of a given power or signal strength and a given measurement time period or may allow a smaller or less powerful source of additional energy to be used for a given SNR and a given measurement time period.

The method may comprise transmitting the additional energy through the electrically non-conductive material of the wall of the fluid conduit as a beam. The use of an electrically non-conductive material in the wall of the fluid conduit may provide further advantages because some portions of the beam of the additional energy may be transmitted through more of the wall of the fluid conduit and less of the fluid flow path. If the fluid conduit was formed from an electrically conductive material, a high power energy beam source and/or a highly sensitive energy beam detector may be required for transmission of such portions of the beam of additional energy across the fluid flow path. In addition, if the fluid conduit was formed from an electrically conductive material, the absorption of the beam of additional energy would be particularly sensitive to any relative movement between any two or more of the energy beam source, the energy beam detector and the electrically conductive fluid conduit and this may have a big impact on calibration. Furthermore, if the fluid conduit was formed from an electrically conductive material, the energy beam source may need to be rated for penetration of the portions of the beam of the additional energy which are transmitted through more of the wall of the fluid conduit and less of the fluid flow path resulting in other portions of the beam of additional energy being transmitted with too much power and resulting in such other portions of the beam of additional energy saturating the corresponding areas of the energy beam detector. This may require different areas of the energy beam detector to have different sensitivities thereby requiring a more complex energy beam detector.

Measuring the additional energy transmitted through the fluid over the measurement time period may comprise measuring the additional energy transmitted into the fluid and measuring the additional energy received from the fluid over the measurement time period.

The additional energy received from the fluid may comprise energy scattered from the fluid.

The fluid conduit may have a transverse cross-section in a plane transverse to the fluid flow path, which transverse cross-section is symmetrical about one or more lines of symmetry.

The method may comprise transmitting a beam of the additional energy across the fluid conduit from a source positioned on one side of the fluid conduit to a detector positioned on the other side of the fluid conduit so that the only area in the transverse plane within the wall which is exposed to the beam of the additional energy is generally defined by one of the one or more lines of symmetry and the wall, and wherein the exposed area constitutes between 40% and 60% of a total area defined by the wall in the transverse plane.

The exposed area may constitute between 45% and 55%, between 49% and 51%, substantially equal to 50%, or 50% of the total area.

The method may comprise transmitting the beam of the additional energy from the source to the detector along a beam axis from the source to the detector along a beam axis which is parallel to, but offset from, the one of the one or more lines of symmetry in the transverse plane.

The method may comprise orienting the fluid conduit such that the fluid flow path is oriented vertically. This may result in a fluid flow regime such that the spatial distribution of the different components of the fluid is symmetrical or approximately symmetrical across the fluid flow path in the transverse plane. For example, the fluid flow path may be circular or generally circular on the transverse plane and the flow regime of the fluid may be such that the spatial distribution of the different components of the fluid may be circularly symmetric or approximately circularly symmetric across the fluid flow path in the transverse plane.

For a flow regime of the fluid which is such that the spatial distribution of the different components of the fluid is symmetrical or approximately symmetrical across the fluid flow path in the transverse plane, the method may permit a value of a characteristic of the fluid to be determined from the measured additional energy transmitted through the fluid over the measurement time period, which value of the characteristic of the fluid is representative of the fluid flowing through the whole of the fluid flow path in the transverse plane. The accuracy of the measurement of the value of the characteristic of the fluid may be improved as the exposed area approaches 50% of the total area defined by the wall in the transverse plane.

Moreover, such a method may allow the source of the beam of the additional energy to be positioned more closely to the fluid conduit compared with the case when the beam of the additional energy is transmitted across the fluid conduit so that the whole of the area defined by the wall in the transverse plane is exposed to the beam. This may result in a more compact arrangement.

In addition, such a method may allow a smaller detector to be used to receive the beam of the additional energy after transmission of the beam of the additional energy across the fluid conduit compared with the case when the beam of the additional energy is transmitted across the fluid conduit so that the whole of the area defined by the wall in the transverse plane is exposed to the beam.

The method may comprise transmitting a beam of the additional energy from a source of the additional energy positioned on one side of the fluid conduit to a detector of the additional energy positioned on the other side of the fluid conduit so that a total area defined by the wall in the transverse plane is exposed to the beam of the additional energy.

Such a method may permit a value of a characteristic of the fluid to be determined from the measured additional energy transmitted through the fluid over the measurement time period, which value of the characteristic of the fluid is representative of the fluid flowing through the whole of the fluid flow path regardless of the fluid flow regime and regardless of the spatial distribution of the different fluid components across the fluid flow path in the transverse plane.

The method may comprise:
using the measured temporal variation in the property of the electromagnetic field and calibration data to estimate a temporal variation of the composition of the fluid; and
using the estimated temporal variation of the composition of the fluid to estimate an average value of a characteristic of the fluid over the measurement time period.

The characteristic of the fluid may comprise a property of the fluid. For example, the characteristic of the fluid may comprise a density of the fluid.

The characteristic of the fluid may comprise gas void fraction.

The characteristic of the fluid may comprise bubble size, bubble count, fluid flow velocity and/or the like.

The method may comprise using the measured additional energy transmitted through the fluid over the measurement time period to determine an independently measured average value of a characteristic of the fluid over the measurement time period.

The method may comprise determining a value of a goal function from the estimated average value of the characteristic of the fluid and the independently measured average value of the characteristic of the fluid.

The goal function value may comprise a difference between the estimated average value of the characteristic of the fluid and the independently measured average value of the characteristic of the fluid.

The method may comprise comparing a magnitude of the goal function value with a predetermined threshold value.

The method may comprise selectively outputting the estimated temporal variation of the composition of the fluid over the measurement time period according to a result of the comparison between the magnitude of the goal function value and the predetermined threshold value.

The method may comprise:
(i) using the measured temporal variation in the property of the electromagnetic field and the calibration data to re-estimate the temporal variation of the composition of the fluid;
(ii) using the re-estimated temporal variation of the composition of the fluid to re-estimate the average value of the characteristic of the fluid over the measurement time period;
(iii) re-determining a value of a goal function from the estimated average value of the characteristic of the fluid and the independently measured average value of the characteristic of the fluid;

(iv) comparing the magnitude of the goal function value with the predetermined threshold value; and
(v) repeating steps (i) to (iv) until the magnitude of the goal function value is less than the predetermined threshold value The fluid flowing through the fluid flow path may comprise at least some liquid during part of the measurement time period and at least some gas during a different part of the measurement time period.

The fluid flowing through the fluid flow path may comprise a higher proportion of liquid than gas during part of the measurement time period and a higher proportion of gas than liquid during a different part of the measurement time period.

The fluid flowing through the fluid flow path may be composed substantially of liquid during part of the measurement time period and may be composed substantially of gas during a different part of the measurement time period.

The composition of the fluid flowing through the fluid flow path may alternate between first and second compositions during the measurement time period.

In the first composition, the fluid may comprise a higher proportion of liquid than gas.

In the first composition, the fluid may be composed substantially of liquid.

In the second composition, the fluid may comprise a higher proportion of gas than liquid.

In the second composition, the fluid may be composed substantially of gas.

The composition of the fluid flowing through the fluid flow path may vary periodically during the measurement time period. For example, the composition of the fluid flowing through the fluid flow path may alternate periodically between the first and second compositions during the measurement time period.

The fluid may flow through the fluid flow path in fluid slugs during the measurement time period, wherein successive fluid slugs are separated by an intervening pocket of fluid, each fluid slug comprises liquid, and each pocket of fluid comprises gas. Each fluid slug may be composed substantially of liquid and each intervening pocket of fluid may be composed substantially of gas.

The fluid flowing through the fluid flow path may comprise bubbles. The bubbles may extend across the fluid flow path.

The method may comprise orienting the fluid conduit so that the fluid flows through the fluid conduit according to a desired flow regime during the measurement time period.

The method may comprise orienting the fluid conduit horizontally. When the fluid conduit is oriented horizontally, the fluid may flow through the fluid flow path in fluid slugs during the measurement time period.

The method may comprise orienting the fluid conduit vertically.

When the fluid conduit is oriented vertically, the fluid flowing through the fluid flow path may comprise Taylor bubbles. Each Taylor bubble may fill the fluid conduit. Each Taylor bubble may travel up through liquid in the fluid flow conduit. This may result in the fluid comprising a higher proportion of gas than liquid during passage of a Taylor bubble through the fluid conduit and a higher proportion of liquid than gas before and after passage of a Taylor bubble.

When the fluid conduit is oriented vertically, the fluid flowing through the fluid flow path may comprise large voids created by churn flow. This may result in the fluid comprising a higher proportion of gas than liquid during passage of a void through the fluid conduit and a higher proportion of liquid than gas before and after passage of a void.

The calibration data may comprise values of the property of the electromagnetic field as a function of gas void fraction and liquid composition over a calibration time period.

The method may comprise measuring the calibration data.

The fluid may comprise water and a further liquid in addition to water. The further liquid may comprise oil. The liquid composition may comprise, or be expressed as, a water-cut value.

The calibration data may comprise the property of the electromagnetic field as a function of gas void fraction and water-cut value.

The calibration data may be single-valued. That is, for each water-cut value and each gas void fraction value, the calibration data may comprise a single value of the property of the electromagnetic field. In effect, such calibration data defines the relationships between three variables, namely the property of the electromagnetic field, the gas void fraction and the water-cut. Such calibration data may be used to determine any one of these three variables from knowledge or a measurement of the other two variables.

The calibration data may comprise a plurality of curves, each curve comprising the property of the electromagnetic field as a function of gas void fraction for a different water-cut value.

The calibration data may comprise a plurality of curves, each curve comprising the property of the electromagnetic field as a function of water-cut for a different gas void fraction value.

The method may comprise:
identifying a recurring feature in the measured temporal variation of the property of the electromagnetic field; and
determining a nominal value of the property of the electromagnetic field associated with the recurring feature.

The recurring feature may comprise at least one of a recurring dip, a recurring reduction, and a recurring local minimum.

The method may comprise selecting the measurement time period according to the number of instances and/or the nature of the recurring feature observed in the measured temporal variation of the property of the electromagnetic field. The method may comprise measuring the property of the electromagnetic field repeatedly until the recurring feature is observed a predetermined number of times.

The method may comprise estimating an initial nominal gas void fraction value associated with the recurring feature.

The method may comprise estimating the initial nominal gas void fraction value to be zero.

The method may comprise using the nominal value of the property of the electromagnetic field and the estimated initial nominal gas void fraction value in conjunction with the calibration data to estimate a nominal composition of any liquid flowing through the fluid conduit over the measurement time period.

The method may comprise using the nominal liquid composition and the calibration data to translate the measured temporal variation of the property of the electromagnetic field into an estimated temporal variation of gas void fraction over the measurement time period.

The nominal liquid composition and the estimated temporal variation of gas void fraction over the measurement time period may together constitute the estimated temporal variation of the composition of the fluid over the measurement time period.

The method may comprise averaging the estimated temporal variation of gas void fraction over the measurement time period to determine the estimated average value of the characteristic of the fluid over the measurement time period.

The method may comprise using the estimated temporal variation of the composition of the fluid over the measurement time period in conjunction with a known value of a property for each fluid component to determine an estimated temporal variation in the property of the fluid over the measurement time period.

The method may comprise averaging the estimated temporal variation in the property of the fluid over the measurement time period to determine the estimated average value of the characteristic of the fluid over the measurement time period.

The method may comprise comparing an estimated value of the property of the fluid with a known value of the property of each of the liquid components of the fluid. For example, the method may comprise comparing an estimated value of the density of the fluid with a known value of the density of each of the liquid components of the fluid.

The method may comprise:
(i) increasing the initial estimate of the gas void fraction value;
(ii) using the nominal value of the property of the electromagnetic field and the estimated initial nominal gas void fraction value in conjunction with the calibration data to estimate a nominal composition of any liquid flowing through the fluid conduit over the measurement time period;
(iii) using the nominal liquid composition and the calibration data to translate the measured temporal variation of the property of the electromagnetic field into an estimated temporal variation of gas void fraction over the measurement time period, the nominal liquid composition and the estimated temporal variation of gas void fraction over the measurement time period constituting an estimated temporal variation of the composition of the fluid over the measurement time period;
(iv) using the estimated temporal variation of the composition of the fluid over the measurement time period in conjunction with a known value of a property for each fluid component to determine an estimated temporal variation in the property of the fluid over the measurement time period; and
(v) comparing an estimated value of the property of the fluid with a known value of the property of each of the liquid components of the fluid; and
(vi) repeating steps (i)-(v) until the estimated value of the property of the fluid lies in a range defined by at least one of the known values of the property for the different liquid components of the fluid.

For example, step (vi) of the method may comprise repeating steps (i)-(v) until the estimated value of the property of the fluid is greater or equal to the known value of the property of one of the liquid components of the fluid.

An apparatus for use in measuring a composition of a multiphase fluid is described herein.

The apparatus may comprise a fluid conduit having a wall defining a fluid flow path for a multiphase fluid.

The wall may comprise an electrically non-conductive material.

The apparatus may comprise an electromagnetic measurement arrangement for establishing an electromagnetic field which extends through the electrically non-conductive material of the wall of the fluid conduit into the fluid and for measuring a property of the electromagnetic field over a measurement time period.

The apparatus may comprise a fluid measurement arrangement for transmitting additional energy through the fluid over the measurement time period independently of the electromagnetic field and measuring the additional energy transmitted through the fluid over the measurement time period.

The apparatus may comprise:

a fluid conduit having a wall defining a fluid flow path for a multiphase fluid, the wall comprising an electrically non-conductive material;

an electromagnetic measurement arrangement for establishing an electromagnetic field which extends through the electrically non-conductive material of the wall of the fluid conduit into the fluid and for measuring a property of the electromagnetic field over a measurement time period; and a fluid measurement arrangement for transmitting additional energy through the fluid over the measurement time period independently of the electromagnetic field and measuring the additional energy transmitted through the fluid over the measurement time period.

Such an apparatus may be used to unambiguously determine a composition of a multiphase fluid which has different components. The apparatus may, in particular, be used to unambiguously determine a water-cut value for a multiphase fluid comprising three components such as oil, water and gas.

Establishing an electromagnetic field which extends through the wall of the fluid conduit into the fluid may provide a relatively uniform electromagnetic field across the fluid flow path. This may help to reduce the sensitivity of a measurement of the property of the electromagnetic field to the distribution of any different fluid components across the fluid flow path. For example, this may help to reduce the sensitivity of a measurement of the resonant frequency of the electromagnetic field to the distribution of any different fluid components across the fluid flow path.

Use of an electrically non-conductive material in the wall of the fluid conduit may allow a stronger electromagnetic field to be established in the fluid compared with use of an electrically conductive material in the wall of the fluid conduit. Use of an electrically non-conductive material in the wall of the fluid conduit may therefore enhance the sensitivity of the measurement of the property of the electromagnetic field compared with use of an electrically conductive material in the wall of the fluid conduit.

The electrically non-conductive material of the wall may define at least part of a thickness of the wall of the fluid conduit.

The electromagnetic field comprises a radio frequency (RF) electromagnetic field.

The property of the electromagnetic field may comprise a resonant frequency of the electromagnetic field.

The additional energy transmitted through the fluid may comprise electromagnetic energy of a different frequency to the electromagnetic field.

The additional energy transmitted through the fluid may comprise gamma radiation.

The additional energy transmitted through the fluid may comprise X-ray radiation.

The additional energy transmitted through the fluid may be of a different type to any energy coupled between the electromagnetic field and the fluid.

The additional energy transmitted through the fluid may comprise acoustic energy.

The fluid conduit may comprise a plurality of sections which are attached together to define the fluid flow path. The electromagnetic field may extend through the electrically non-conductive material of the wall of one section into the fluid, and the additional energy may be transmitted through the fluid flowing through a portion of the fluid flow path defined by a wall of a different section of the fluid conduit.

The wall of the fluid conduit may be formed from the electrically non-conductive material.

The electrically non-conductive material may comprise a polymer material.

The electrically non-conductive material may comprise a polyether ether ketone (PEEK) material.

The wall may comprise an inner sleeve.

The wall may comprise one or more layers formed one on top of the other around the inner sleeve.

The wall may comprise an outer sleeve which is assembled over the inner sleeve.

The outer sleeve may be integrally formed or may be unitary.

The outer sleeve may define a hole through which the inner sleeve extends.

The outer sleeve may comprise a first U-shaped member and a second U-shaped member. The first and second U-shaped members may be bonded, adhered, fused, welded and/or joined together so as to define the outer sleeve.

The outer sleeve may comprise a plurality of members, each member having a pair of parallel sides and defining a hole extending through the member from one of the parallel sides to the other parallel side, wherein the plurality of members are configured for assembly over the inner sleeve such that the inner sleeve extends through the hole of each member and a parallel side of each member engages a parallel side of an adjacent member. Each member of the outer sleeve may be generally annular. The members of the outer sleeve may be bonded, adhered, fused, welded and/or joined together so as to define the outer sleeve.

The electromagnetic measurement arrangement may comprise a confinement arrangement for at least partially confining the electromagnetic field.

The confinement arrangement may be located externally of the fluid conduit.

The confinement arrangement may be at least partially enclosed within the wall of the fluid conduit.

The confinement arrangement may be at least partially embedded within the wall of the fluid conduit.

The confinement arrangement may comprise an electrically conductive material.

The confinement arrangement may comprise a composite material including a matrix material and one or more reinforcing elements embedded within the matrix material.

The matrix material may be electrically non-conductive.

The one or more reinforcing elements may be electrically conductive.

The confinement arrangement may comprise a polyether ether ketone (PEEK) material and one or more carbon fibre reinforcing elements embedded within the PEEK material.

The wall of the fluid conduit may comprise the same matrix material as the composite material of the confinement arrangement.

The wall of the fluid conduit may be substantially devoid of any reinforcing elements. Such a wall may be more transparent to the electromagnetic field and/or to the additional energy transmitted through the fluid independently of the electromagnetic field.

The matrix material of the composite material of the confinement arrangement may be continuous with the matrix material of the wall of the fluid conduit. This may provide a mechanically strong fluid conduit. Such a fluid conduit may be capable of withstanding relatively high internal and/or external pressures. Such a fluid conduit may also be substantially devoid of any gaps or voids between the confinement arrangement and the wall of the fluid conduit. This may be important so as to avoid any loss of pressure integrity through the wall of the fluid conduit.

The confinement arrangement and the wall of the fluid conduit may be integrally formed.

The confinement arrangement may be formed on or around the wall of the fluid conduit.

The confinement arrangement may comprise a metal.

The confinement arrangement may be configured to establish the electromagnetic field across the fluid flow path.

The confinement arrangement may define a resonant cavity for the electromagnetic field through which the fluid flow path extends.

The resonant cavity may include the electrically non-conductive material of the wall of the fluid conduit.

The confinement arrangement may comprise a cavity member which is separately formed from the wall of the fluid conduit through which the electromagnetic field extends.

The electromagnetic measurement arrangement may comprise one or more components for coupling energy to and/or from the electromagnetic field.

Each of the one or more components for coupling energy to and/or from the electromagnetic field may comprise an antenna.

Each of the one or more components of the electromagnetic measurement arrangement may comprise at least one of a transducer, a transmitter, a source, a receiver and a detector.

Each of the one or more components of the electromagnetic measurement arrangement may be located internally of the confinement arrangement.

Each of the one or more components for coupling energy to and/or from the electromagnetic field may be at least partially embedded in and/or at least partially enclosed within the electrically non-conductive material of the wall of the fluid conduit.

The electromagnetic measurement arrangement may comprise an electrical signal generator for providing electrical energy to the one or more components of the electromagnetic measurement and an electrical signal detector for receiving electrical energy from the one or more components of the electromagnetic measurement.

The fluid measurement arrangement may comprise one or more components for transmitting the additional energy through the fluid and/or receiving the additional energy after transmission through the fluid.

Each of the one or more components of the fluid measurement arrangement may comprise at least one of a transducer, an antenna, a transmitter, a source, a receiver and a detector.

The additional energy may comprise gamma radiation and/or gamma-rays.

The additional energy may comprise X-ray radiation and/or X-rays.

The additional energy may comprise acoustic energy.

The fluid conduit may have a transverse cross-section on a plane transverse to the fluid flow path, which transverse cross-section is symmetrical about one or more lines of symmetry.

The fluid measurement arrangement may comprise:
a source of a beam of the additional energy positioned on one side of the fluid conduit; and
a detector of the beam of the additional energy positioned on the other side of the fluid conduit,
wherein the source and the detector are arranged relative to the fluid conduit for the transmission of the beam of the additional energy across the fluid conduit from the source to the detector so that the only area in the transverse plane within the wall which is exposed to the beam of the additional energy is generally defined by one of the one or more lines of symmetry and the wall, and wherein the exposed area constitutes between 40% and 60% of a total area defined by the wall in the transverse plane.

The exposed area may constitute between 45% and 55%, between 49% and 51%, substantially equal to 50%, or 50% of the total area.

The source and the detector may be arranged relative to the fluid conduit for the transmission of the beam of the additional energy from the source to the detector along a beam axis which is parallel to, but offset from, the one of the one or more lines of symmetry in the transverse plane.

The fluid measurement arrangement may comprise:
a source of a beam of the additional energy positioned on one side of the fluid conduit; and
a detector of the beam of the additional energy positioned on the other side of the fluid conduit,
wherein the source and the detector are arranged relative to the fluid conduit for the transmission of the beam of the additional energy from the source to the detector so that a total area defined by the wall in the transverse plane is exposed to the beam of the additional energy.

The wall may comprise an electrically non-conductive material.

The wall may be formed from an electrically non-conductive material.

The source and the detector may be arranged relative to the fluid conduit for the transmission of the beam of the additional energy through the electrically non-conductive material.

The fluid measurement arrangement may be configured for transmitting the additional energy through the electrically non-conductive material of the wall of the fluid conduit in addition to the fluid over the measurement time period and for measuring the additional energy transmitted through the electrically non-conductive material of the wall of the fluid conduit and the fluid over the measurement time period.

Transmitting the additional energy through the wall of the fluid conduit may permit a transmitter and/or receiver of the additional energy to be located externally of the wall of the fluid conduit or to be at least partially embedded and/or at least partially enclosed within the wall of the fluid conduit so that the transmitter and/or receiver do not protrude or extend into the fluid flow path. Transmitting the additional energy through the wall of the fluid conduit may avoid any requirement to form or define an aperture which extends through the wall of the fluid conduit. Consequently, the wall may have improved strength and/or pressure integrity.

Transmitting the additional energy through the electrically non-conductive material of the wall of the fluid conduit may serve to reduce the measurement time period required to measure the additional energy transmitted through the fluid for a given source of the additional energy and for a given signal-to-noise ratio (SNR) compared with transmitting the additional energy through an electrically conductive material. Conversely, transmitting the additional energy through the electrically non-conductive material of the wall of the fluid conduit may increase the SNR achieved for a given source of additional energy and a given measurement time period or may allow a smaller or less powerful source of additional energy to be used for a given SNR and a given measurement time period.

The one or more components of the fluid measurement arrangement may be located internally of the confinement arrangement.

The one or more components of the fluid measurement arrangement may be at least partially embedded in and/or at least partially enclosed within the electrically non-conductive material of the wall of the fluid conduit.

The one or more components of the fluid measurement arrangement may be located externally of the electrically non-conductive material of the wall of the fluid conduit.

A method is described herein for use in measuring a characteristic of a multiphase fluid, the method comprising:

providing a fluid conduit having a wall defining a fluid flow path, the fluid conduit having a transverse cross-section in a plane transverse to the fluid flow path, which transverse cross-section is symmetrical about one or more lines of symmetry;

flowing a multiphase fluid through the fluid conduit;

transmitting a beam of energy across the fluid conduit from a source positioned on one side of the fluid conduit to a detector positioned on the other side of the fluid conduit so that the only area in the transverse plane within the wall which is exposed to the beam of energy is generally defined by one of the one or more lines of symmetry and the wall, and wherein the exposed area constitutes between 40% and 60% of a total area defined by the wall in the transverse plane.

The exposed area may constitute between 45% and 55%, between 49% and 51%, substantially equal to 50%, or 50% of the total area.

The method may comprise transmitting the beam of energy from the source to the detector along a beam axis which is parallel to, but offset from, the one of the one or more lines of symmetry in the transverse plane.

The beam of energy may comprise electromagnetic energy.

The beam of energy may comprise gamma radiation and/or gamma-rays.

The beam of energy may comprise X-ray radiation and/or X-rays.

The beam of energy may comprise acoustic energy.

The method may comprise measuring a value of a property of the beam of energy received by the detector.

The property of the beam of energy may comprise at least one of a power, intensity and signal strength of the beam of energy.

The property of the beam of energy may comprise a phase and/or a frequency of the beam of energy.

The method may comprise determining a characteristic of the fluid such as a density or composition of the fluid from the measured value of the property of the received beam of energy.

The method may comprise measuring a value of the property of the beam of energy before transmission of the beam of energy across the fluid conduit.

The method may comprise determining a difference between the value of the property of the received beam of energy after transmission of the beam of energy across the fluid conduit and the value of the property of the beam of energy before transmission of the beam of energy across the fluid conduit.

The method may comprise determining a property of the fluid such as a density or composition of the fluid from the determined difference between the value of the property of the beam of energy received by the detector after transmission of the beam of energy across the fluid conduit and the value of the property of the beam of energy before transmission of the beam of energy across the fluid conduit.

The method may comprise orienting the fluid conduit such that the fluid flow path is oriented vertically. This may result in a fluid flow regime such that the spatial distribution of the different components of the fluid is symmetrical or approximately symmetrical across the fluid flow path in the transverse plane. For example, the cross-section of the fluid flow path may be circular or generally circular and the flow regime of the fluid may be such that the spatial distribution of the different components of the fluid may be circularly symmetric or approximately circularly symmetric across the fluid flow path in the transverse plane.

For a flow regime of the fluid which is such that the spatial distribution of the different components of the fluid is symmetrical or approximately symmetrical across the fluid flow path in the transverse plane, the value of the property of the beam of energy received by the detector using the method may be the same as, or approximately equal to, the value of the property of the beam of energy when the whole of the area defined by the wall in the transverse plane is exposed to the beam of energy.

For a flow regime of the fluid which is such that the spatial distribution of the different components of the fluid is symmetrical or approximately symmetrical across the fluid flow path in the transverse plane, the method may permit a value of a characteristic of the fluid to be measured which is representative of the fluid flowing through the whole of the fluid flow path in the transverse plane.

Moreover, the method may allow a source of the beam of energy to be positioned more closely to the fluid conduit compared with the case when the whole of the area defined by wall in the transverse plane is exposed to the beam of energy. This may result in a more compact arrangement.

In addition, the method may allow a smaller detector to be used to measure the value of the property of the beam of energy after transmission of the beam of energy across the fluid conduit compared with the case when the whole of the area defined by wall in the transverse plane is exposed to the beam of energy.

The wall may comprise an electrically non-conductive material.

The wall may be formed from the electrically non-conductive material.

The method may comprise transmitting the beam of energy through the electrically non-conductive material.

The electrically non-conductive material may comprise a polymer material.

The electrically non-conductive material may comprise a polyether ether ketone (PEEK) material.

Use of an electrically non-conductive material in the wall of the fluid conduit may serve to reduce the measurement time period for an energy beam source of a given power or signal strength and for a given signal-to-noise ratio (SNR) compared with use of an electrically conductive material for the wall of the fluid conduit. Conversely, use of an electrically non-conductive material in the wall of the fluid conduit may increase the SNR achieved for an energy beam source of a given power or signal strength and a given measurement time period or may allow a smaller or less powerful energy beam source to be used for a given SNR and a given measurement time period.

Moreover, use of an electrically non-conductive material in the wall of the fluid conduit may provide further advantages because some portions of the beam of energy may be transmitted across the fluid conduit through more of the wall of the fluid conduit and less of the fluid flow path. If the fluid conduit was formed from an electrically conductive material, a high power energy beam source and/or a highly sensitive energy beam detector may be required for transmission of such portions of the beam of energy from one side of the fluid conduit to the other side of the fluid conduit across the fluid flow path. In addition, if the fluid conduit was formed from an electrically conductive material, the absorption of the beam of energy would be particularly sensitive to any relative movement between two or more of the energy beam source, the energy beam detector and the electrically conductive fluid conduit and this may have a big impact on calibration. Furthermore, if the fluid conduit was formed from an electrically conductive material, the energy beam source may need to be rated for penetration of such portions of the beam of energy through the fluid conduit resulting in other portions of the beam of energy which are transmitted through less of the wall of the fluid conduit and more of the fluid flow path being transmitted with too much power and resulting in such other portions of the beam of energy saturating the corresponding areas of the energy beam detector. This may require different areas of the energy beam detector to have different sensitivities thereby requiring a more complex energy beam detector.

Transmitting the beam of energy across the fluid conduit may comprise transmitting the beam of energy through the fluid in the fluid flow path.

Transmitting the beam of energy across the fluid conduit may comprise scattering the beam of energy from the fluid in the fluid flow path.

An apparatus is described herein for use in measuring a characteristic of a multiphase fluid, the apparatus comprising:

a fluid conduit having a wall defining a fluid flow path for a multiphase fluid, the fluid conduit having a transverse cross-section in a plane transverse to the fluid flow path, which transverse cross-section is symmetrical about one or more lines of symmetry;

a source of a beam of energy positioned on one side of the fluid conduit; and a detector of the beam of energy positioned on the other side of the fluid conduit, wherein the source and the detector are arranged relative to the fluid conduit for transmission of the beam of energy across the fluid conduit from the source to the detector so that the only area in the transverse plane within the wall which is exposed to the beam of energy is generally defined by one of the one or more lines of symmetry and the wall, and wherein the exposed area constitutes between 40% and 60% of a total area defined by the wall in the transverse plane.

The exposed area may constitute between 45% and 55%, between 49% and 51%, substantially equal to 50%, or 50% of the total area.

The source and the detector may be arranged relative to the fluid conduit for transmission of the beam of energy from the source to the detector along a beam axis which is parallel to, but offset from, the one of the one or more lines of symmetry in the transverse plane.

The cross-section of the fluid flow path may be circular or generally circular.

The transmitter and/or receiver of the beam of energy may be located externally of the wall of the fluid conduit or may be at least partially embedded and/or be at least partially enclosed within the wall of the fluid conduit so that the transmitter and/or receiver do not protrude or extend into the fluid flow path. This may avoid any requirement to form or define an aperture which extends through the wall of the fluid conduit. Consequently, the wall may have improved strength and/or pressure integrity.

The wall may comprise an electrically non-conductive material.

The wall may be formed from the electrically non-conductive material.

The source and the detector may be arranged relative to the fluid conduit for the transmission of the beam of energy through the electrically non-conductive material.

The electrically non-conductive material may comprise a polymer material.

The electrically non-conductive material may comprise a polyether ether ketone (PEEK) material.

BRIEF DESCRIPTION OF THE DRAWINGS

Methods and apparatus for the measurement of a composition of a fluid are described by way of non-limiting example only with reference to the following figures of which.

DETAILED DESCRIPTION OF THE DRAWINGS

Figure 1:
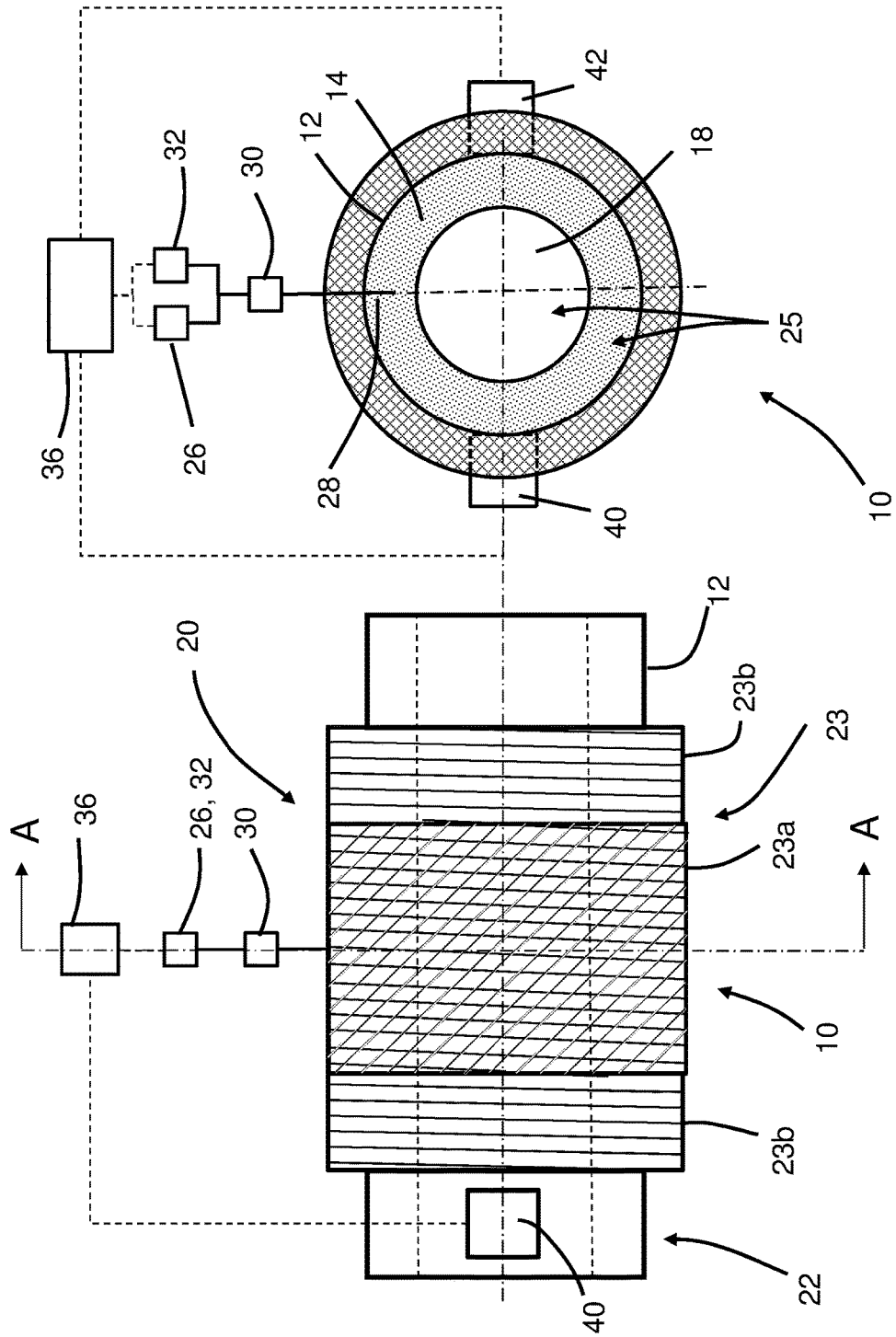
FIG. 1A shows a schematic side view of an apparatus for use in measuring a composition of a fluid.
FIG. 1B is a transverse cross-section on AA of the apparatus of FIG. 1A.

Referring initially to FIGS. 1A and 1B there is shown an apparatus generally designated 10 for use in measuring a composition of a fluid. The apparatus 10 includes a fluid conduit 12 having a wall 14 which defines a fluid flow path 18. The wall 14 is formed from an electrically non-conductive polyether ether ketone (PEEK) material. The apparatus 10 further includes an electromagnetic measurement arrangement generally designated 20 and a fluid measurement arrangement in the form of a gamma densitometer generally designated 22.

The electromagnetic measurement arrangement 20 includes an electrically conductive confinement arrangement 23 formed on an outer surface of the wall 14 of the fluid conduit 12. The confinement arrangement 23 comprises a composite material formed from a polyether ether ketone (PEEK) matrix material and one or more carbon fibre reinforcing elements embedded within the PEEK matrix material. The PEEK matrix material of the confinement arrangement 23 is continuous with the PEEK material of the wall 14 of the fluid conduit 12. The confinement arrangement 23 comprises an axially central portion 23a and axial end portions 23b located either end of the axially central portion 23a. The carbon fibres within the axially central portion 23a of the confinement arrangement 23 are generally helically aligned around the fluid conduit 12 at different angles. The carbon fibres within the axially end portions 23b of the confinement arrangement 23 are generally circumferentially aligned.

It should be understood that the confinement arrangement 23 defines a resonant cavity 25 for confinement of a radio frequency (RF) electromagnetic field extending from the confinement arrangement 23 through the wall 14 of the fluid conduit 12 and across the fluid flow path 18. The particular arrangement of carbon fibres in the axially central portion 23a and the axially end portions 23b of the confinement arrangement 23 serves to confine electromagnetic energy within the cavity 25. The PEEK material of the wall 14 of the fluid conduit 12 is relatively transparent to the radio frequency (RF) electromagnetic field. The thickness of the wall 14 is selected to provide the electromagnetic field with a relative uniform distribution across the fluid flow path 18. This may help to reduce the sensitivity of a measurement of a property of the electromagnetic field to a non-uniform distribution of any different fluid components across the fluid flow path 18. For example, this may help to reduce the sensitivity of a measurement of a resonant frequency of the electromagnetic field to a non-uniform distribution of any different fluid components across the fluid flow path 18.

The electromagnetic measurement arrangement 20 further includes an RF electrical signal generator 26 electrically connected to an antenna 28 via a circulator device 30 and an RF electrical signal detector 32 which is also electrically connected to the antenna 28 via the circulator device 30. The antenna 28 extends through the confinement arrangement 23 into the wall 14 of the fluid conduit 12. The antenna 28 is electrically isolated from the confinement arrangement 23.

The gamma densitometer 22 is axially separated from the confinement arrangement 23. The gamma densitometer 22 includes a gamma radiation source 40 and a gamma radiation detector 42. The gamma radiation source 40 and the gamma radiation detector 42 are attached to the outer surface of the wall 14 of the fluid conduit 12. The gamma radiation source 40 and the gamma radiation detector 42 are arranged so that the gamma radiation detector 42 may detect any gamma radiation transmitted from the gamma radiation source 40 through any fluid flowing through the fluid flow path 18.

Figure 8A:
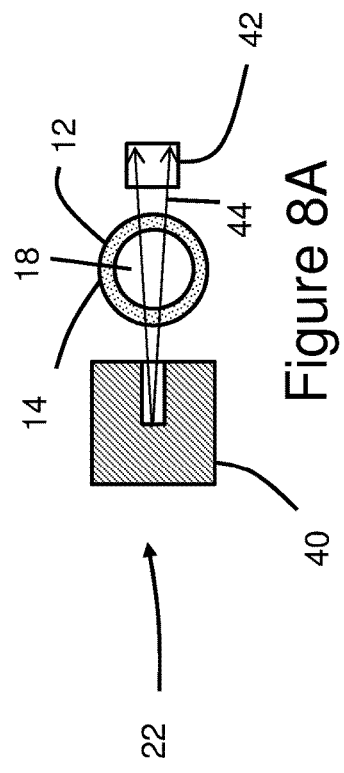
FIG. 8A shows a transverse cross-section of a first gamma densitometer arrangement for use with the apparatus of FIG. 1A.

FIG. 8A shows a first arrangement of the gamma densitometer 22. Although not shown explicitly in FIG. 8A, it should be understood that the gamma radiation source 40 and the gamma radiation detector 42 may be attached to the outer surface of the wall 14 of the fluid conduit 12. The gamma radiation source 40 and the gamma radiation detector 42 are arranged so that, in use, the gamma radiation source 40 emits a gamma-ray beam 44 which is transmitted through a first side of the wall 14 of the fluid conduit 12 into the fluid flow path 18, through any fluid flowing through the fluid flow path 18 and out of the fluid flow path 18 through a second side of the wall 14 of the fluid conduit 12 onto the gamma radiation detector 42.

As shown in FIG. 8A, the gamma-ray beam 44 and gamma radiation detector 42 are much smaller than the fluid conduit 12 so that, in use, the gamma densitometer arrangement 22 only measures the density of a fluid passing through the area in the transverse plane which is exposed to the gamma-ray beam 44 and which extends generally across a diameter of the fluid conduit 12. Consequently, the density measured using the first arrangement of the gamma densitometer 22 shown in FIG. 8A is only generally representative of the average density of the fluid flowing through the whole fluid flow path 18 when the distribution of the different components of the fluid flowing through the exposed area is generally representative of the distribution of the different components of the fluid flowing through the whole fluid flow path 18. In practice, however, it has been found that the density measured using the first arrangement of the gamma densitometer 22 shown in FIG. 8A is only approximately representative of the average density of the fluid flowing through the whole fluid flow path 18 if the distribution of the different fluid components across the fluid flow path 18 is circularly symmetric. This is one of the reasons that some known multiphase meters (not shown) may include one or more flow structures such as one or more vanes or the like in the fluid flow path to create a swirl in the fluid so as to create circular symmetry. However, inserting such flow structures in the fluid flow path 18 of the apparatus 10 may impact on fluid flow and, in really chaotic or slugging flows, may still not create the desired degree of circular symmetry.

Figure 8B:
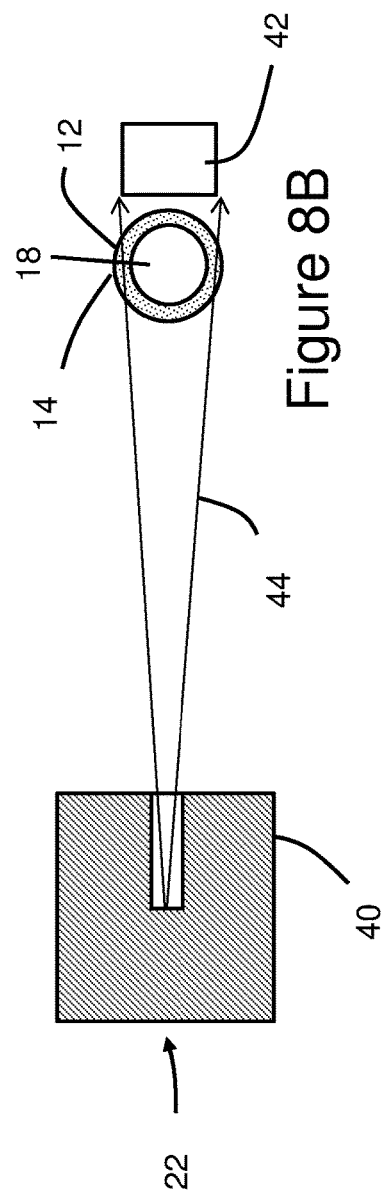
FIG. 8B shows a transverse cross-section of a second gamma densitometer arrangement for use with the apparatus of FIG. 1A.

FIG. 8B shows a second arrangement of the gamma densitometer 22. Although not shown explicitly in FIG. 8A, it should be understood that the gamma radiation source 40 and the gamma radiation detector 42 may be attached to the outer surface of the wall 14 of the fluid conduit 12. The gamma radiation source 40 and the gamma radiation detector 42 are arranged so that, in use, the gamma radiation source 40 emits a gamma-ray beam 44 which is transmitted through a first side of the wall 14 of the fluid conduit 12 into the fluid flow path 18, through any fluid flowing through the fluid flow path 18 and out of the fluid flow path 18 through a second side of the wall 14 of the fluid conduit 12 onto the gamma radiation detector 42.

Unlike the first arrangement shown in FIG. 8A, in the second arrangement shown in FIG. 8B, the whole of the fluid flow path 18 is exposed to the gamma-ray beam 44 such that the fluid density measured by the gamma densitometer arrangement 22 of FIG. 8B is representative of a density of the fluid flowing through the whole fluid flow path 18 regardless of the distribution of the different fluid components across the fluid flow path 18. Consequently, use of the second gamma densitometer arrangement 22 of FIG. 8B may avoid any requirement to insert any flow structures in the fluid flow path 18.

Moreover, the uppermost and lowermost portions of the gamma-ray beam 44 are transmitted through more of the wall 14 of the fluid conduit 12 and less of the fluid flow path 18. If the fluid conduit 12 was formed from of a material which was less transparent to gamma radiation such as steel, the gamma-ray beam 44 would have to be sufficiently powerful for transmission of the uppermost and lowermost portions of the gamma-ray beam 44 through the wall 14 of the fluid conduit 12 into the fluid flow path 18, through the fluid, and through the wall 14 of the fluid conduit 12. In addition, if the fluid conduit 12 was formed from a material which was less transparent to gamma radiation such as steel, the absorption of the gamma-ray beam 44 would be particularly sensitive to any relative movement between two or more of the gamma radiation source 40, the gamma radiation detector 42 and the fluid conduit 12 and this may have a big impact on calibration. Furthermore, if the fluid conduit 12 was formed from a material which was less transparent to gamma radiation such as steel and the gamma radiation source 40 was rated to ensure penetration of the uppermost and lowermost portions of the gamma-ray beam 44 through the wall 14 of the fluid conduit 12, the middle portion of the gamma-ray beam 44 transmitted through the middle of the fluid conduit 12 where the gamma-ray beam 44 is transmitted through less of the wall 14 of the fluid conduit 12 and more of the fluid flow path 18 may be much greater. This may require the gamma radiation detector 42 to have a less sensitive middle area for receiving the middle portion of the gamma-ray beam 44 and more sensitive uppermost and lowermost areas for receiving the uppermost and lowermost portions of the gamma-ray beam 44 respectively to stop the gamma radiation detector 42 from becoming saturated. This would require a more complex gamma radiation detector 42. However, all of these issues associated with the use of a fluid conduit 12 formed from a material which is less transparent to gamma radiation such as steel may be eliminated by forming the fluid conduit from a material which is more transparent to gamma radiation such as PEEK such that the relative absorption of the uppermost and lowermost portions of the gamma-ray beam 44 is not materially different from the relative absorption of the middle portion of the gamma-ray beam 44.

It should be understood that for the second arrangement of the gamma densitometer 22 shown in FIG. 8B, the gamma radiation detector 42 generally needs to be larger than the fluid conduit 12 itself and the gamma radiation source 40 has to be placed some distance away from the fluid conduit 12. This results in the second gamma densitometer arrangement 22 of FIG. 8B being generally larger than the gamma densitometer arrangement 22 of FIG. 8A. This may make it more difficult to mount the gamma densitometer arrangement 22 of FIG. 8B around the fluid conduit 12.

Figure 8C:
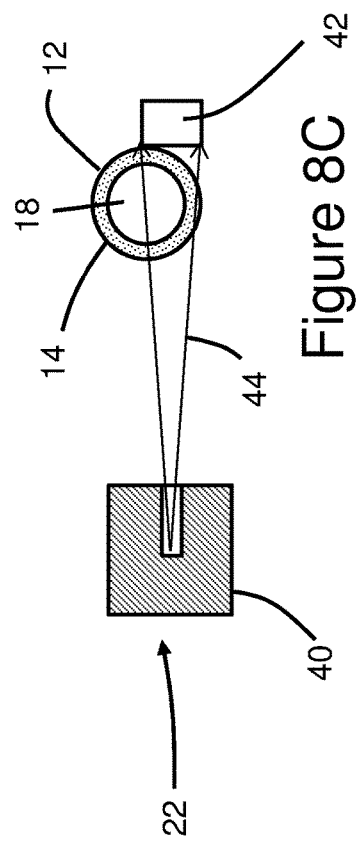
FIG. 8C shows a transverse cross-section of a third gamma densitometer arrangement for use with the apparatus of FIG. 1A.

Such mounting difficulties may be at least partially mitigated using the third arrangement of the gamma densitometer 22 shown in FIG. 8C. Although not shown explicitly in FIG. 8C, it should be understood that the gamma radiation source 40 and the gamma radiation detector 42 may be attached to the outer surface of the wall 14 of the fluid conduit 12. The gamma radiation source 40 and the gamma radiation detector 42 are arranged so that, in use, the gamma radiation source 40 emits a gamma-ray beam 44 which is transmitted through a first side of the wall 14 of the fluid conduit 12 into the fluid flow path 18, through any fluid flowing through the fluid flow path 18, out of the fluid flow path 18 through a second side of the wall 14 of the fluid conduit 12 and onto the gamma radiation detector 42.

Unlike the second arrangement shown in FIG. 8B, in the third arrangement shown in FIG. 8C, the gamma-ray beam 44 is transmitted across the fluid conduit so that the only area in the transverse plane within the wall 14 which is exposed to the gamma-ray beam 44 is generally defined by a diameter of the fluid conduit 12 and the wall 14. The exposed area may constitute between 40% and 60%, between 45% and 55%, between 49% and 51%, substantially equal to 50%, or 50%, of the total area defined by the wall 14 in the transverse plane. Experiments have demonstrated that the fluid density measured by the gamma densitometer arrangement 22 of FIG. 8C may be representative of a density of the fluid flowing through the whole of the fluid flow path 18 when the distribution of the different fluid components across the fluid flow path 18 exhibits mirror symmetry across the diameter of the fluid flow path 18 with the accuracy of the fluid density measurements improving as the exposed area approaches 50% of the total area defined by the wall 14 in the transverse plane. This is particularly true when the fluid conduit 12 is oriented vertically. Consequently, use of the second gamma densitometer arrangement 22 of FIG. 8B may not only avoid any requirement to insert any flow structures in the fluid flow path 18 to induce circular symmetry, but may also essentially half the size of the gamma radiation detector 42 required and essentially half the spacing between the gamma radiation source 40 and the fluid conduit 12.

It should be understood that because the PEEK material of the wall 14 of the fluid conduit 12 is relatively transparent to gamma radiation, the amount of gamma radiation detected by the gamma radiation detector 42 is higher than the amount of gamma radiation that would otherwise be detected by the gamma radiation detector 42 if the wall 14 were formed of a material which is less transparent to gamma radiation such as steel. In particular, for a given amount of gamma radiation emitted from the gamma radiation source 40, the amount of gamma radiation detected by the gamma radiation detector 42 is significantly higher than the amount of gamma radiation that would otherwise be detected by the gamma radiation detector 42 if the wall 14 were formed of a material which is less transparent to gamma radiation such as steel. As described in more detail below, this can have important consequences when it is necessary for the gamma radiation detector 42 to acquire measurements over a measurement period, for example by counting and averaging gamma scintillations. More specifically, use of an electrically non-conductive material such as PEEK for the wall 14 may reduce the measurement period required for a given gamma radiation source 40 and a given gamma radiation signal to noise ratio (SNR) compared with use of an electrically conductive material for the wall 14. Conversely, the use of an electrically non-conductive material such as PEEK for the wall 14 may increase the gamma radiation SNR achieved for a given gamma radiation source 40 and a given measurement period or may allow a smaller or less powerful gamma radiation source 40 to be used for a given gamma radiation SNR and a given measurement period.

Referring back to FIGS. 1A and 1B, the apparatus 10 further includes a controller 36 which is in communication with the electrical signal generator 26, the electrical signal detector 32, the gamma radiation source 40 and the gamma radiation detector 42.

In use, the multiphase fluid flowing through the fluid flow path 18 may include one or more liquids and one or more gases. The fluid may, in particular, include oil, water and gas. It should be understood that the relative proportions of the different components of the multiphase fluid varies over time. In particular, it should be understood that the fluid flowing through the fluid flow path 18 comprises at least some liquid during part of a measurement time period and at least some gas during a different part of the measurement time period. Such a flow regime is typical or characteristic of a multiphase fluid flow. When the fluid conduit 12 is oriented horizontally, the fluid may flow predominantly in slugs through the fluid flow path 18 during the measurement time period, wherein successive fluid slugs are separated by an intervening pocket of fluid, each fluid slug comprises liquid, and each pocket of fluid comprises gas. For example, each fluid slug may be composed substantially of liquid and each intervening pocket of fluid may be composed substantially of gas. The distribution of the different components of the fluid across the fluid flow path 18 may be non-uniform or non-homogenous. The method for use in measuring the composition of the fluid flowing through the fluid flow path 18 described in more detail below makes no assumptions about the particular distribution of the different components of the fluid across the fluid flow path 18. More specifically, the method described in more detail below does not require the different fluid components flowing through the fluid flow path 18 to be uniformly distributed or deliberately mixed before flowing through the fluid flow path 18.

As the fluid flows through the fluid flow path 18, the controller 36 determines a property of the electromagnetic field from an electrical signal generated by the electrical signal generator 26 and an electrical signal detected by the electrical signal detector 32. In particular, the controller 36 determines a resonant frequency of the electromagnetic field from the electrical signal generated by the electrical signal generator 26 and the electrical signal detected by the electrical signal detector 32 using conventional electrical measurement techniques. Such electrical measurement techniques may, for example, involve sweeping a frequency of an electrical signal generated by the electrical signal generator 26 and measuring the electrical signal detected by the electrical signal detector 32 as a function of the frequency of the generated electrical signal. The controller 36 repeatedly determines the resonant frequency of the electromagnetic field in this way over a measurement time period so as to provide a temporal variation in the resonant frequency of the electromagnetic field. The controller 36 also determines the absorption of gamma radiation in the fluid flowing through the fluid flow path 18 from the gamma densitometer 22 over the measurement time period.

Before the apparatus 10 is used to measure the composition of an unknown fluid flowing through the fluid flow path 18, the apparatus 10 is calibrated by measuring the resonant frequency of the electromagnetic field for different known fluid compositions flowing through the fluid flow path 18. For example, before the apparatus 10 is used to measure a composition of a mixture of oil, water and gas flowing through the fluid flow path 18 in unknown proportions, the apparatus 10 is calibrated by measuring the resonant frequency of the electromagnetic field for different known proportions of oil, water and gas flowing through the fluid flow path 18. During calibration, a mixture of oil, water and gas having a known water-cut value but an unknown GVF is introduced into the fluid flow path 18. The controller 36 controls the electrical signal generator 26 and the electrical signal detector 32 so as to measure the resonant frequency of the electromagnetic field repeatedly over a measurement time period and the controller 36 averages the measured resonant frequencies to determine an average resonant frequency of the electromagnetic field over the measurement time period.

The controller 36 further controls the gamma densitometer 22 so as to measure gamma absorption over the same measurement time period. The controller 36 determines an average density for the fluid flowing through the fluid flow path 18 over the measurement time period from the measured average gamma absorption and from calibration data for the gamma densitometer 22 which is stored in the controller 36. The controller 36 then uses the average density for the fluid flowing through the fluid flow path 18, the respective known densities of the oil, water and gas in the fluid flow path 18, and the known water-cut value to determine a GVF value corresponding to the average resonant frequency of the electromagnetic field. Without varying the water-cut value of the fluid introduced into the fluid flow path 18, a flow rate of the gas introduced into the fluid flow path 18 is varied and the controller 36 determines an average resonant frequency of the electromagnetic field and a GVF value for different gas flow rates. Once the average resonant frequencies and the GVF values have been determined for an appropriate range of GVF values, the water-cut is varied and the controller 36 determines the average resonant frequencies of the electromagnetic field and the GVF values for different gas flow rates across the same range of GVF values. The resulting calibration data is stored in the controller 36. It should be understood that the calibration data obtained using the procedure described above is essentially constant for a measurement time period of sufficient duration i.e. the calibration data is essentially independent of the measurement time period for measurement time periods of sufficient duration.

Figure 2:
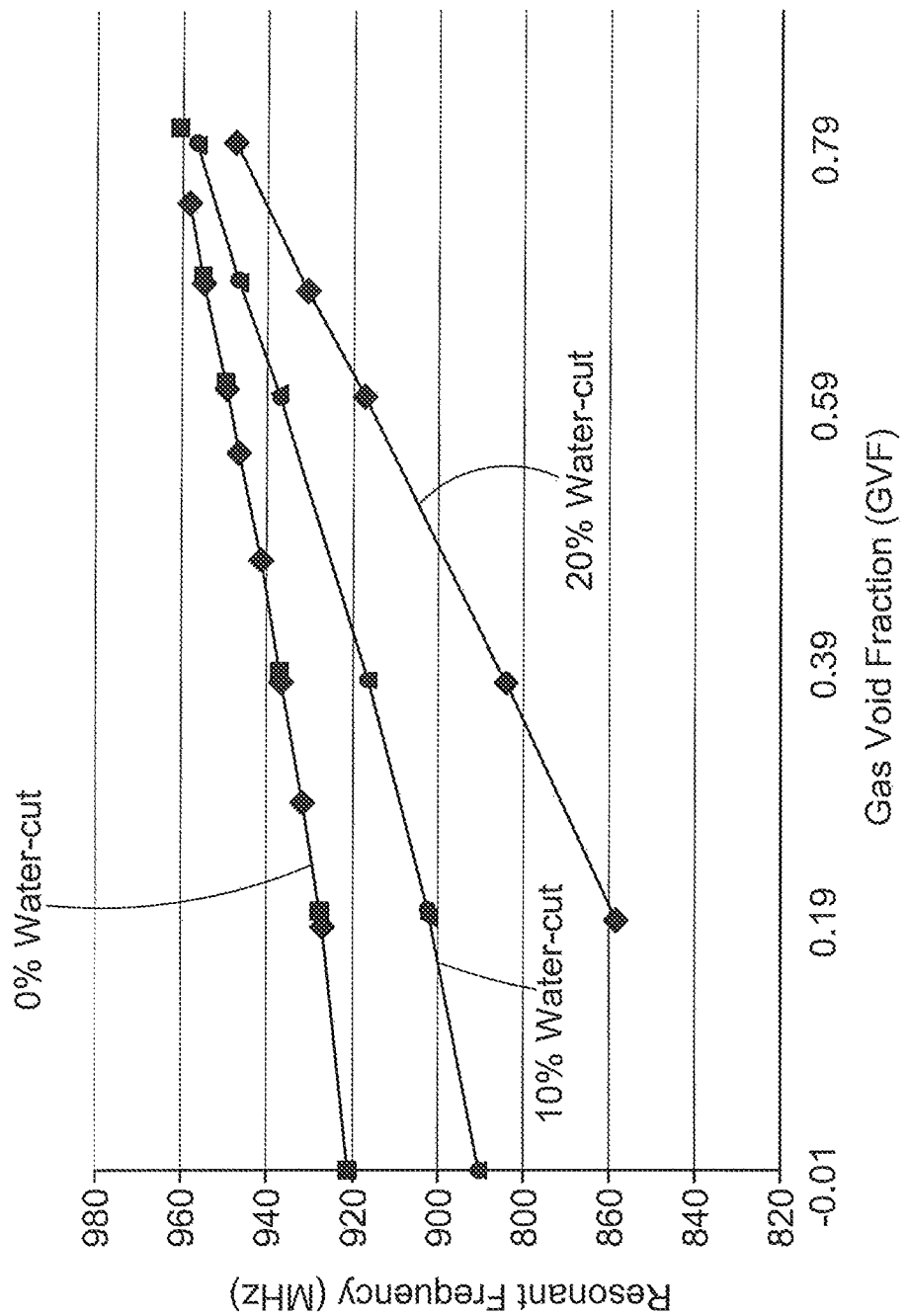
FIG. 2 shows empirical calibration data measured for different known fluid compositions flowing through the fluid conduit of the apparatus of FIGS. 1A and 1B.

FIG. 2 shows the calibration data obtained using the calibration procedure described above for a mixture of oil, water and gas flowing through the fluid flow path 18. It should be understood that the calibration data of FIG. 2 is essentially independent of the particular flow regime of the fluid flowing through the fluid flow path 18 during the measurement time period. Without wishing to be bound by theory, this is thought to be a consequence of the generally uniform distribution of the electromagnetic field across the fluid flow path 18.

One of ordinary skill in the art will understand that the calibration data of FIG. 2 is single-valued. That is, for each water-cut value and each gas void fraction value, the calibration data comprises a single value of the resonant frequency of the electromagnetic field. In effect, such calibration data defines the relationships between three variables, namely the resonant frequency of the electromagnetic field, the gas void fraction and the water-cut, and may be used to determine any one of these three variables from knowledge or a measurement of the other two variables.

Figure 3:
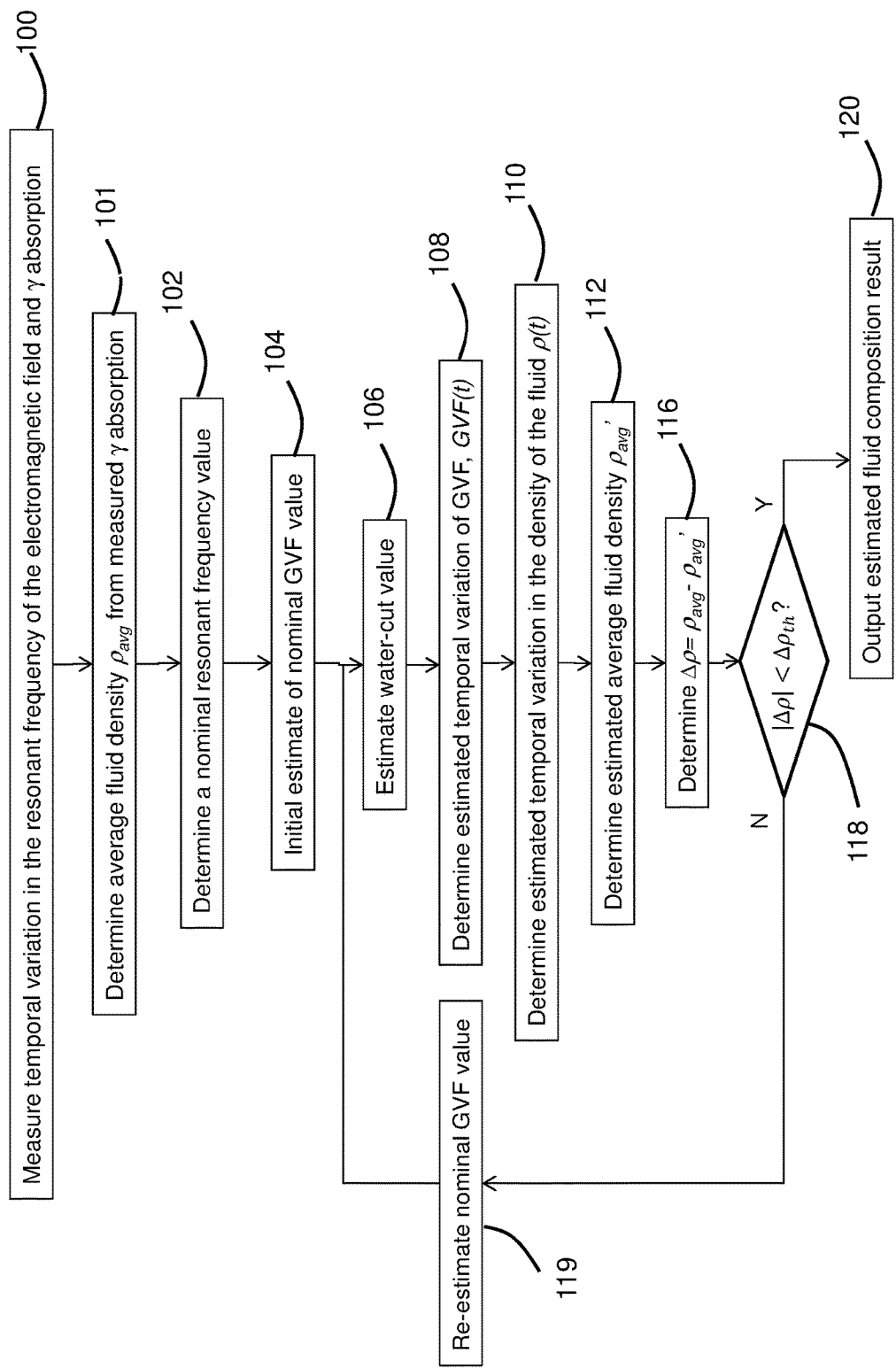
FIG. 3 is a flow chart illustrating a method for estimating a fluid composition using the apparatus of FIGS. 1A and 1B.

Once calibration is complete, the apparatus 10 is used to measure the time-varying composition of a fluid comprising oil, water and gas using the method described with reference to FIG. 3. At step 100, the controller 36 controls the electrical signal generator 26 and the electrical signal detector 32 so as to measure the resonant frequency of the electromagnetic field repeatedly over a measurement time period as the fluid flows through the fluid flow path 18 until two or more recurring local features such as two or more recurring local minima are observed in the measured temporal variation of the resonant frequency of the electromagnetic field. At step 100, the controller 36 also controls the gamma densitometer 22 so as to measure the gamma absorption over the same measurement time period.

At step 101, the controller 36 determines an average density $\rho_{avg}$ for the fluid flowing through the fluid flow path 18 from the gamma absorption measured over the measurement time period and calibration data for the gamma densitometer 22 stored in the controller 36.

Figure 4:
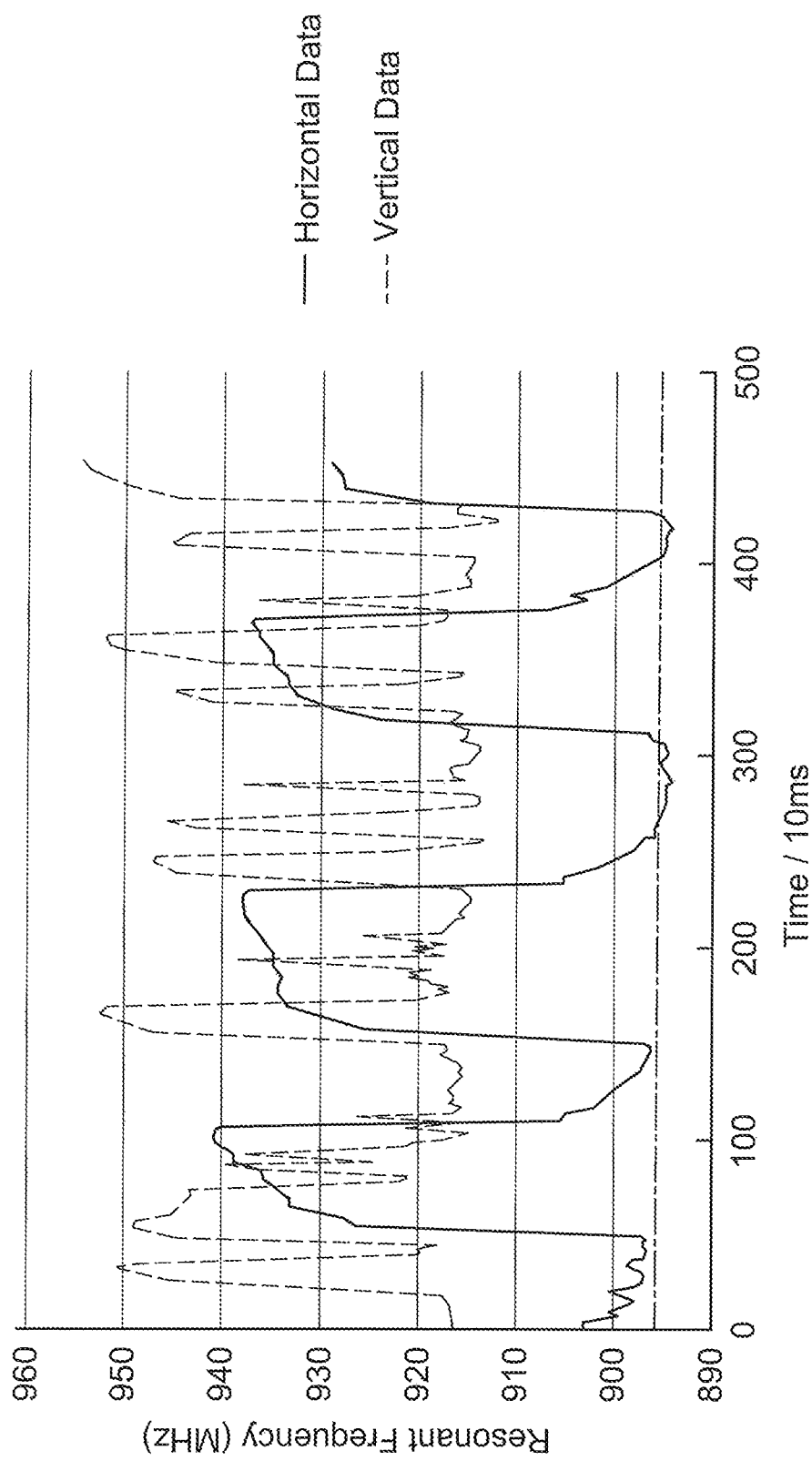
FIG. 4 shows the measured temporal variation in a resonant frequency of an electromagnetic field during the flow of a fluid having a time-varying composition through a fluid conduit of the apparatus of FIGS. 1A and 1B for different orientations of the fluid conduit.

The temporal variation in the resonant frequency of the electromagnetic field measured at step 100 is plotted in blue in FIG. 4. The obvious recurring local minima in the measured temporal variation of the resonant frequency of the electromagnetic field plotted in blue in FIG. 4 are thought to correspond to the flow of fluid slugs composed substantially of liquid through the fluid flow path 18, wherein the different slugs comprise a liquid having a generally similar or invariant water-cut value. Such a flow regime may be typical for fluids produced from an oil or gas well.

At step 102, the controller 36 identifies the recurring local minima in the measured temporal variation of the resonant frequency of the electromagnetic field and determines a nominal value of the resonant frequency of the electromagnetic field associated with the recurring local minima. For the temporal variation of the resonant frequency of the electromagnetic field shown in FIG. 4, the controller 36 determines the nominal value of the resonant frequency of the electromagnetic field associated with the recurring local minima to be approximately 895 MHz. Since the recurring local minima in the measured temporal variation of the resonant frequency of the electromagnetic field plotted in blue in FIG. 4 are thought to correspond to the flow of fluid slugs composed substantially of liquid through the fluid flow path 18 wherein the different slugs comprise a liquid having a generally similar or invariant water-cut value, the controller 36 initially estimates a nominal GVF value of zero for the fluid slugs at step 104 in FIG. 3.

At step 106, the controller 36 uses the nominal value of 895 MHz of the resonant frequency of the electromagnetic field and the estimated nominal GVF value in conjunction with the calibration data of FIG. 2 to estimate a nominal composition of the fluid slugs flowing through the fluid flow path 18. More specifically, the controller 36 uses the calibration data of FIG. 2 to estimate the water-cut value corresponding to the nominal value of the resonant frequency of the electromagnetic field of 895 MHz and the estimated nominal GVF value.

At step 108, the controller 36 uses the estimated water-cut value and the calibration data of FIG. 2 to translate the measured temporal variation of the resonant frequency of the electromagnetic field plotted in blue in FIG. 4 into an estimated temporal variation of GVF, GVF(t), over the measurement time period. It should be understood that the estimated water-cut value and the estimated temporal variation of GVF, GVF(t), together constitute the estimated temporal variation of the composition of the fluid flowing through the fluid flow path 18 during the measurement time period.

At step 110, the controller 36 uses the estimated water-cut value and GVF(t) over the measurement time period in conjunction with the respective known densities of the oil, water and gas to determine an estimated temporal variation in the density $\rho(t)$ of the fluid flowing through the fluid flow path 18 over the measurement time period.

At step 112, the controller 36 determines an estimated average value of the density of the fluid $\rho_{avg}'$ over the measurement time period by averaging the estimated temporal variation in the density $\rho(t)$ of the fluid over the measurement time period.

At step 116, the controller 36 determines a goal function in the form of a difference $\Delta\rho$ between the estimated average value of the density of the fluid $\rho_{avg}'$ and the independently measured average value of the density of the fluid $\rho_{avg}$ which was determined by the controller 36 from the gamma absorption measurements at step 101.

At step 118, the controller 36 compares a magnitude of $\Delta\rho$ to a predetermined difference value $\Delta\rho_{th}$.

If the controller 36 determines that the magnitude of $\Delta\rho$ is less than the predetermined difference value $\Delta\rho_{th}$ at step 118, the method ends at step 120 with the controller 36 outputting the estimated composition of the fluid flowing through the fluid flow path 18 to a user or operator of the apparatus 10. More specifically, the controller 36 outputs the estimated water-cut value and the estimated temporal variation of GVF, GVF(t), over the measurement time period to a user or operator of the apparatus 10.

If the controller 36 determines that the magnitude of $\Delta\rho$ is greater than or equal to the predetermined difference value $\Delta\rho_{th}$, this may indicate that the fluid slugs which correspond to the recurring local minima in the measured temporal variation of the resonant frequency of the electromagnetic field plotted in blue in FIG. 4 are not composed solely of liquid but may comprise a relatively small fraction of gas. Accordingly, if the magnitude of $\Delta\rho$ is greater than or equal to the predetermined difference value $\Delta\rho_{th}$, the controller 36 re-estimates a nominal value for the GVF at step 119. More specifically, at step 119, the controller 36 compares the magnitude and/or sign of $\Delta\rho$ determined during one iteration of step 116 with the magnitude and/or sign of $\Delta\rho$ determined during a later iteration of step 116 and re-estimates the nominal GVF value at step 119 according to the result of the comparison. The controller 36 subsequently repeats steps 106 through 118 until the magnitude of $\Delta\rho$ is less than the predetermined difference value $\Delta\rho_{th}$ at step 118.

Figure 5:
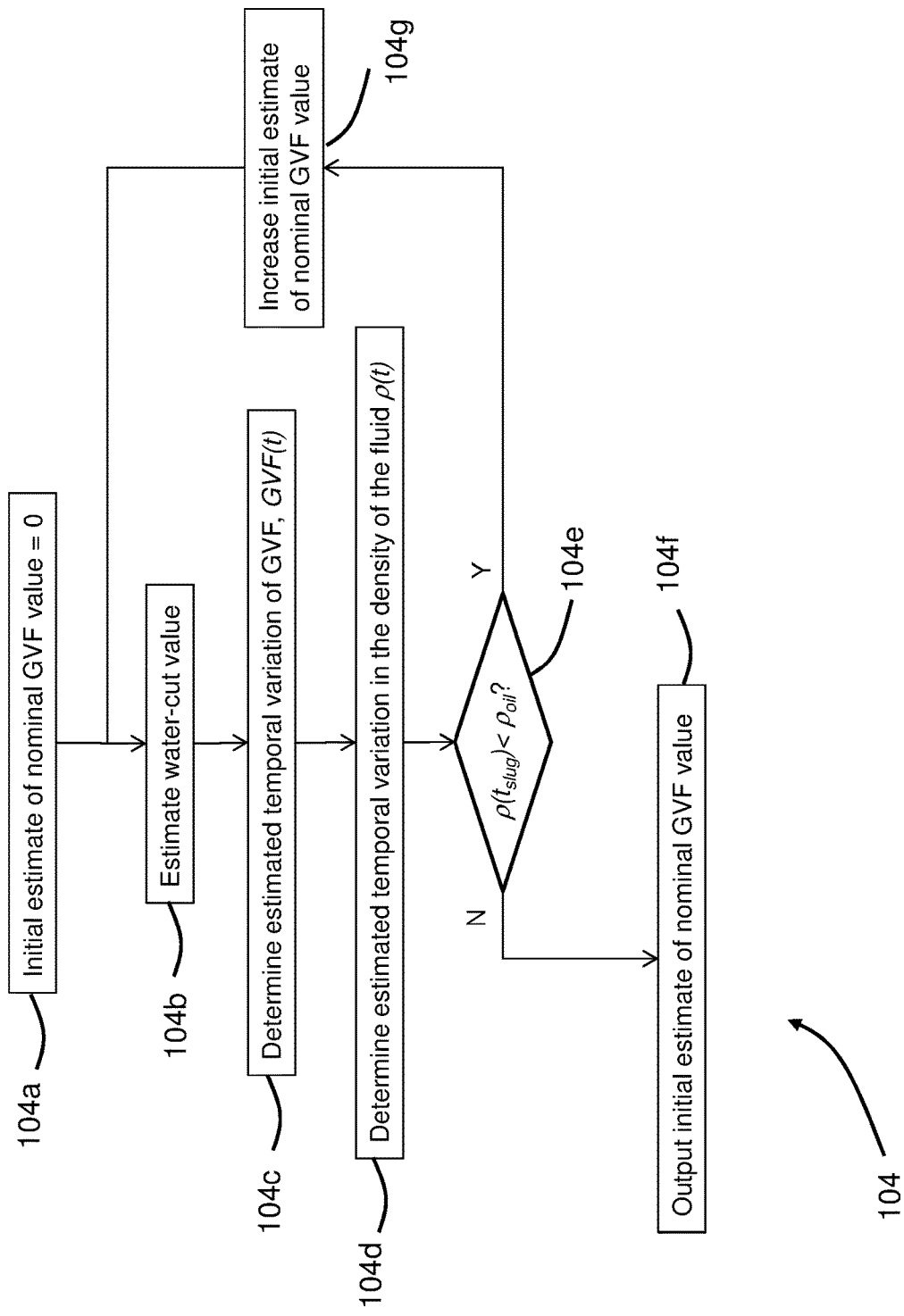
FIG. 5 is a flow chart illustrating a refinement of step 104 of the method for estimating a fluid composition of FIG. 4.

FIG. 5 illustrates a refinement of step 104. At step 104a, the controller 36 estimates a nominal GVF value of zero. Steps 104b, 104c and 104d are identical to steps 106, 108 and 110 respectively. At step 104e, the controller 36 determines the density $\rho(t)$ determined at a time or times $t=t_{slug}$ corresponding to one or more of the recurring local minima of FIG. 4 and compares the density $\rho(t_{slug})$ with a minimum density $\rho_{oil}$ for oil. If the controller 36 determines that $\rho(t_{slug}) < \rho_{oil}$ this is indicative that the fluid flowing through the fluid flow path 18 at $t=t_{slug}$ contains some gas and that the initial estimate of zero for the nominal GVF value at $t=t_{slug}$ was too low. Accordingly, the controller 36 increases the initial estimate of the nominal GVF value at step 104g and repeats steps 104b, 104c, 104d and 104e until the controller 36 determines that $\rho(t_{slug}) \geq \rho_{oil}$ at step 104e whereupon the initial estimate of the nominal GVF value is provided at step 104f.

Figures 6A, 6B:
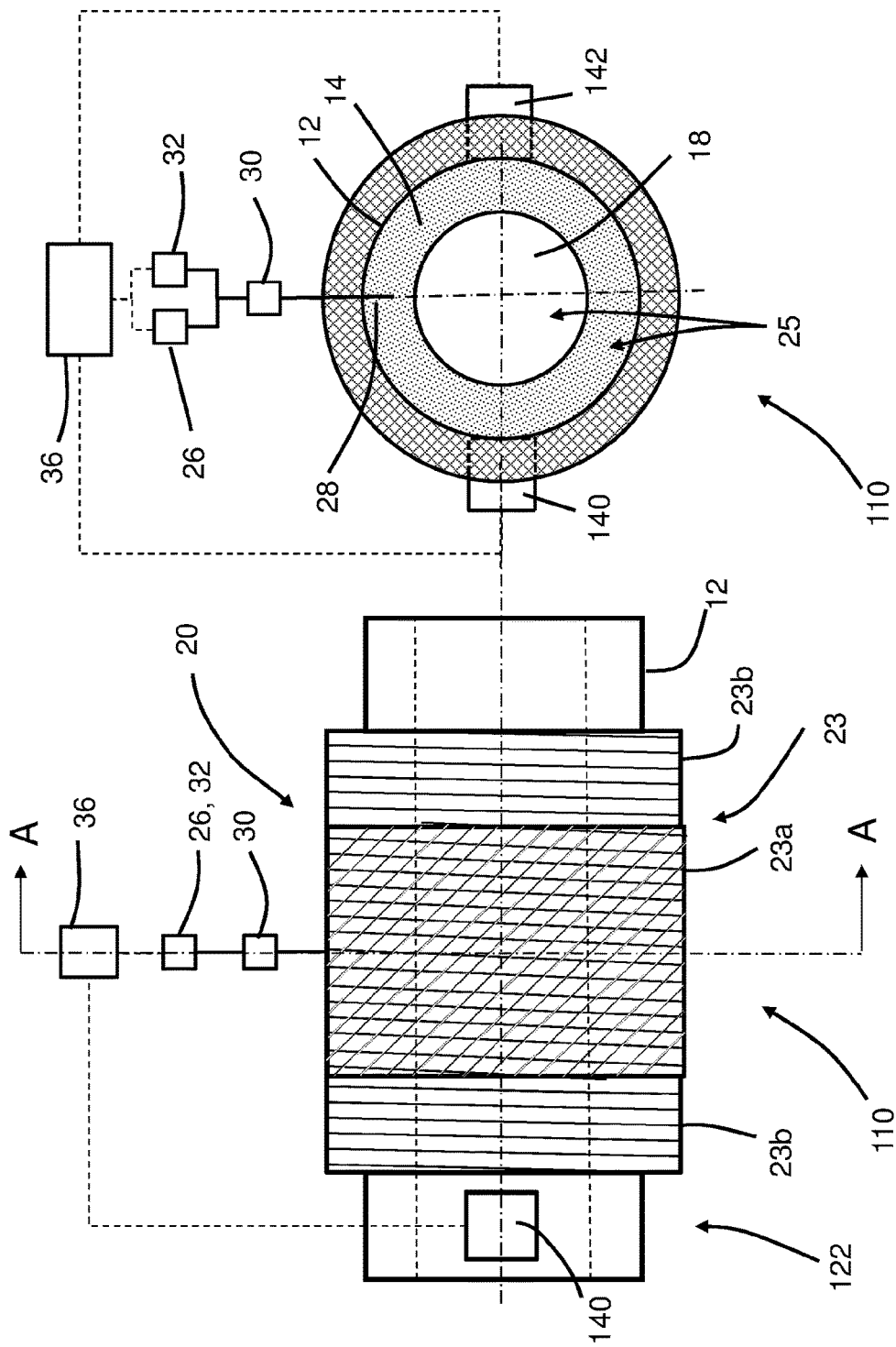
FIG. 6A shows a schematic side view of an alternative apparatus for use in measuring a composition of a fluid.
FIG. 6B is a transverse cross-section on AA of the apparatus of FIG. 6A.

An alternative apparatus 110 for use in measuring a composition of a fluid is shown in FIGS. 6A and 6B. The only difference between the apparatus 110 and the apparatus 10 is that apparatus 110 comprises an acoustic energy measurement arrangement 122 in place of the gamma densitometer 22 of apparatus 10. As shown in FIG. 6B, the acoustic energy measurement arrangement 122 comprises an acoustic source 140 in place of the gamma radiation source 40 and an acoustic detector 142 in place of the gamma radiation detector 42. The acoustic source 140 may be arranged to transmit acoustic energy through the fluid flow path 18 and the controller 36 may be arranged to determine an average characteristic of the fluid in the fluid flow path 18 from the acoustic energy received by the acoustic detector 142. For example, the controller 36 may be arranged to determine the average gas void fraction from the acoustic energy transmitted by the acoustic source 140 and/or the acoustic energy received by the acoustic detector 142.

During calibration of the apparatus 110 a mixture of oil, water and gas having a known water-cut value but an unknown GVF is introduced into the fluid flow path 18. The controller 36 controls the electrical signal generator 26 and the electrical signal detector 32 so as to measure the resonant frequency of the electromagnetic field repeatedly over a measurement time period and the controller 36 averages the measured resonant frequencies to determine an average resonant frequency of the electromagnetic field over the measurement time period.

The controller 36 also controls the acoustic source 140 and the acoustic detector 142 so as to measure the transmission of acoustic energy through the fluid over the measurement time period. The controller 36 determines an average GVF value for the fluid flowing through the fluid flow path 18 over the measurement time period from the measured average transmission of acoustic energy through the fluid and from calibration data for the acoustic energy measurement arrangement 122 which is stored in the controller 36. Without varying the water-cut value of the fluid introduced into the fluid flow path 18, a flow rate of the gas introduced into the fluid flow path 18 is varied and the controller 36 determines an average resonant frequency of the electromagnetic field and an average GVF value for different gas flow rates. Once an average resonant frequency and an average GVF value has been determined for an appropriate range of average GVF values, the water-cut is varied and the controller 36 determines an average resonant frequency of the electromagnetic field and an average GVF for different gas flow rates across the same range of GVF values. The resulting calibration data is stored in the controller 36. It should be understood that the calibration data obtained using the apparatus 110 according to the calibration procedure outlined above resembles that shown in FIG. 2 measured using the apparatus 10.

Figure 7:
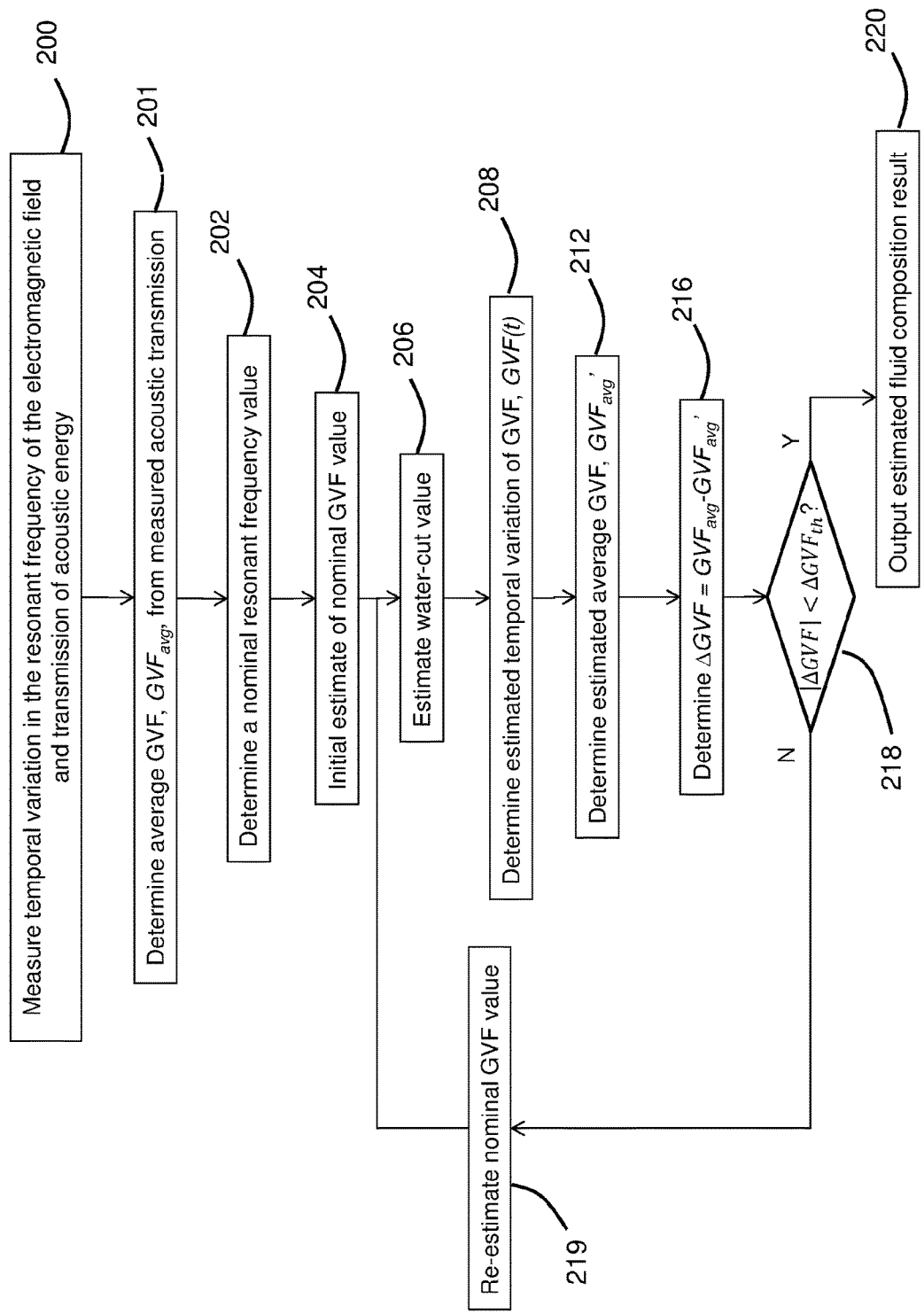
FIG. 7 is a flow chart illustrating a method for estimating a fluid composition using the apparatus of FIGS. 6A and 6B.

Once calibration is complete, the apparatus 110 may be used to measure a composition of a mixture of oil, water and gas flowing through the fluid flow path 18 in unknown proportions using the method described with reference to FIG. 7. At step 200, the controller 36 controls the electrical signal generator 26 and the electrical signal detector 32 so as to measure the resonant frequency of the electromagnetic field repeatedly over a measurement time period as the fluid flows through the fluid flow path 18 until two or more recurring local features such as two or more recurring local minima are observed in the measured temporal variation of the resonant frequency of the electromagnetic field. At step 200, the controller 36 also controls the acoustic energy measurement arrangement 122 so as to measure the transmission of acoustic energy over the same measurement time period.

At step 201, the controller 36 determines an average GVF value, $GVF_{avg}$, for the fluid flowing through the fluid flow path 18 from the transmission of acoustic energy measured over the measurement time period and the calibration data for the acoustic energy measurement arrangement 122 stored in the controller 36. The temporal variation in the resonant frequency of the electromagnetic field measured at step 200 is the same as that plotted in blue in FIG. 4. As such, steps 202, 204, 206 and 208 are effectively identical to steps 102, 104, 106 and 108 described with reference to FIG. 3.

At step 208, the controller 36 uses the estimated water-cut value and the calibration data of FIG. 2 to translate the measured temporal variation of the resonant frequency of the electromagnetic field plotted in blue in FIG. 4 into an estimated temporal variation of GVF, GVF(t), over the measurement time period. It should be understood that the estimated water-cut value and the estimated temporal variation of GVF, GVF(t), together constitute the estimated temporal variation of the composition of the fluid flowing through the fluid flow path 18 during the measurement time period.

At step 212, the controller 36 determines an estimated average GVF value, $GVF_{avg}'$, over the measurement time period by averaging GVF(t) over the measurement time period.

At step 216, the controller 36 determines a goal function in the form of a difference ΔGVF between the estimated average GVF value, $GVF_{avg}'$, and the independently measured average GVF value, $GVF_{avg}$, determined by the controller 36 from the acoustic transmission measurement at step 201.

At step 218, the controller 36 subsequently compares a magnitude of ΔGVF to a predetermined difference value $\Delta GVF_{th}$.

If the controller 36 determines that the magnitude of ΔGVF is less than the predetermined difference value $\Delta GVF_{th}$ at step 218, the method ends at step 220 with the controller 36 outputting the estimated fluid composition to a user or operator of the apparatus 110.

If the controller 36 determines that the magnitude of ΔGVF is greater than or equal to the predetermined difference value $\Delta GVF_{th}$, this may indicate that the fluid slugs which correspond to the recurring local minima in the measured temporal variation of the resonant frequency of the electromagnetic field plotted in blue in FIG. 4 are not composed solely of liquid but may comprise a relatively small fraction of gas. Accordingly, if the magnitude of ΔGVF is greater than or equal to the predetermined difference value $\Delta GVF_{th}$, the controller 36 re-estimates a nominal value for the GVF at step 219. More specifically, at step 219, the controller 36 compares the magnitude and/or sign of ΔGVF determined during one iteration of step 216 with the magnitude and/or sign of ΔGVF determined during a later iteration of step 216 and re-estimates the nominal GVF value at step 219 according to the result of the comparison. The controller 36 subsequently repeats steps 206 through 218 until the magnitude of ΔGVF is less than the predetermined difference value $\Delta GVF_{th}$ at step 218.

One of ordinary skill in the art will appreciate that various modifications of the apparatus and methods described above may be made. For example, the apparatus 10 or the apparatus 110 may comprise both a gamma densitometer and an acoustic energy transmission arrangement. Furthermore, although the method described with reference to FIG. 3 was based upon measuring an average density using the gamma densitometer 22 and comparing the measured average density with an estimated average density determined from measurements of the resonant frequency of the electromagnetic field, the method may instead comprise measuring an average GVF value using the gamma densitometer 22 and comparing the measured average GVF value with an estimated average GVF value determined from measurements of the resonant frequency of the electromagnetic field. More specifically, rather than determining an average density value, $\rho_{avg}$, from the measured gamma absorption at step 101 of FIG. 3 and comparing $\rho_{avg}$ at step 116 with an estimated average density value, $\rho_{avg}'$, determined from measurements of the resonant frequency of the electromagnetic field as described with reference to steps 102-112 of FIG. 3, the controller 36 may determine an average GVF value, $GVF_{avg}$, from the measured gamma absorption at step 101 and compare $GVF_{avg}$ at step 116 with an estimated average GVF value, $GVF_{avg}'$, determined from measurements of the resonant frequency of the electromagnetic field as described with reference to steps 202-212 of FIG. 7.

Conversely, although the method described with reference to FIG. 7 was based upon measuring an average GVF value using the acoustic measurement arrangement 122 and comparing the measured average GVF value with an estimated average GVF value determined from measurements of the resonant frequency of the electromagnetic field, the method may instead comprise measuring an average density using the acoustic measurement arrangement 122 and comparing the measured average density with an estimated average density determined from measurements of the resonant frequency of the electromagnetic field. More specifically, rather than determining an average GVF value, $GVF_{avg}$, from the measured acoustic transmission at step 201 of FIG. 7 and comparing $GVF_{avg}$ at step 216 with an estimated average GVF value, $GVF_{avg}'$, determined from measurements of the resonant frequency of the electromagnetic field as described with reference to steps 202-212 of FIG. 7, the controller 36 may determine an average density value, $\rho_{avg}$, from the measured acoustic transmission at step 201 and compare $\rho_{avg}$ at step 216 with an estimated average density value, $\rho_{avg}'$, determined from measurements of the resonant frequency of the electromagnetic field as described with reference to steps 102-112 of FIG. 3.

The fluid conduit 12 may be oriented vertically during calibration and measurement. As discussed above, this may result in a more symmetrical distribution of the different fluid components in the fluid flow path 18. The resulting measured temporal variation in the resonant frequency of the electromagnetic field is plotted in red in FIG. 4. Although the resulting temporal variation in the resonant frequency of the electromagnetic field has recurring local minima, these are less pronounced than the recurring local minima in the temporal variation in the resonant frequency of the electromagnetic field when the fluid conduit 12 is oriented horizontally as shown in blue in FIG. 4. Put another way, when the fluid conduit 12 is oriented vertically, although the fluid may flow through the fluid flow path in fluid slugs during the measurement time period with successive fluid slugs separated by an intervening pocket of fluid, each fluid slug may comprise a mixture of liquid and gas, and each intervening pocket of fluid may comprise a mixture of liquid and gas, wherein the proportion of liquid is greater in each fluid slug compared with the proportion of liquid in each intervening pocket of fluid. This may be the consequence of bubbles such as Taylor bubbles or voids moving upwardly through the liquid in the fluid flow path 18.

The confinement arrangement may comprise an electrically conductive layer or an electrically conductive member of any kind. For example, the confinement arrangement may be formed of metal. The confinement arrangement may be at least partially embedded within the wall 14 of the fluid conduit 12. The confinement arrangement may be integrally formed with the wall 14 of the fluid conduit 12. The confinement arrangement may be formed on or around the wall 14 of the fluid conduit 12.

The gamma radiation source 40 and the gamma radiation detector 42 may be at least partially embedded within the wall 14 of the fluid conduit 12.

The wall 14 of the fluid conduit 12 may comprise different axial sections, wherein different axial sections have different diameters.

The confinement arrangement 23 may comprise different axial sections, wherein different axial sections have different diameters.

The confinement arrangement 23 may have different carbon fibre orientations to those described above.

The controller may be arranged to determine other characteristics of the fluid such as bubble size, bubble count, fluid flow velocity and/or the like from the additional energy transmitted through the fluid. For example, the controller may be arranged to determine such other characteristics of the fluid from a measurement of absorption of gamma radiation in the fluid and/or from a measurement of transmission of acoustic energy through the fluid.

The apparatus may comprise at least one of a pressure sensor and a temperature sensor. The controller may be configured to correct at least one of a measured RF resonance frequency, measured gamma radiation absorption and measured acoustic transmission according to a pressure measured by the pressure sensor and/or a temperature measured by the temperature sensor.

The invention claimed is:

1. A method for use in measuring a composition of a multiphase fluid, the method comprising:
    flowing a multiphase fluid through a fluid flow path defined by a wall of a fluid conduit, the wall comprising an electrically non-conductive material;
    establishing an electromagnetic field which extends through the electrically non-conductive material of the wall of the fluid conduit into the fluid;
    measuring a property of the electromagnetic field over a measurement time period so as to provide a measured temporal variation in the property of the electromagnetic field;
    transmitting additional energy through the fluid over the measurement time period independently of the electromagnetic field; and
    measuring the additional energy transmitted through the fluid over the measurement time period; and
    comprising confining the electromagnetic field in a resonant cavity through which the fluid flow path extends,
    wherein the electromagnetic field comprises a radio frequency (RF) electromagnetic field and wherein the property of the electromagnetic field comprises a resonant frequency of the electromagnetic field, wherein the fluid conduit has a transverse cross-section in a plane transverse to the fluid flow path, which transverse cross-section is symmetrical about one or more lines of symmetry, and the method additionally comprises:
    transmitting a beam of the additional energy across the fluid conduit from a source positioned on one side of the fluid conduit to a detector positioned on the other side of the fluid conduit so that the only area in the transverse plane within the wall which is exposed to the beam of the additional energy is generally defined by one of the one or more lines of symmetry and the wall, and wherein the exposed area constitutes between 40% and 60% of a total area defined by the wall in the transverse plane.

2. The method according to claim 1, comprising establishing the electromagnetic field across the fluid flow path.

3. The method according to claim 1, wherein the resonant cavity includes the electrically non-conductive material of the wall of the fluid conduit.

4. The method according to claim 1, wherein the additional energy transmitted through the fluid comprises electromagnetic energy of a different frequency to the electromagnetic field.

5. The method according to claim 1, wherein the additional energy transmitted through the fluid comprises at least one of gamma radiation, gamma-rays, X-ray radiation and X-rays.

6. The method according to claim 1, wherein the additional energy transmitted through the fluid is of a different type to any energy coupled between the electromagnetic field and the fluid.

7. The method according to claim 1, wherein the additional energy transmitted through the fluid comprises acoustic energy.

8. The method according to claim 1, comprising:
    transmitting the additional energy through the electrically non-conductive material of the wall of the fluid conduit; and measuring the additional energy transmitted through the fluid and the electrically non-conductive material of the wall of the fluid conduit over the measurement time period.

9. The method according to claim 1, wherein measuring the additional energy transmitted through the fluid over the measurement time period comprises measuring additional energy transmitted into the fluid and measuring additional energy received from the fluid over the measurement time period.

10. The method according to claim 1, wherein the additional energy received from the fluid comprises energy scattered from the fluid.

11. The method according to claim 1, wherein the exposed area constitutes between 45% and 55%, between 49% and 51%, substantially equal to 50%, or 50% of the total area.

12. The method according to claim 1, comprising transmitting the beam of the additional energy from the source to the detector along a beam axis from the source to the detector along a beam axis which is parallel to, but offset from, the one of the one or more lines of symmetry in the transverse plane.

13. The method according to claim 1, comprising:
using the measured temporal variation in the property of the electromagnetic field and calibration data to estimate a temporal variation of the composition of the fluid; and
using the estimated temporal variation of the composition of the fluid to estimate an average value of a characteristic of the fluid over the measurement time period.

14. The method according to claim 13, wherein the characteristic of the fluid comprises a property of the fluid.

15. The method according to claim 13, wherein the characteristic of the fluid comprises a density of the fluid.

16. The method according to claim 13, wherein the characteristic of the fluid comprises a gas void fraction of the fluid.

17. The method according to claim 13, wherein the characteristic of the fluid comprises at least one of bubble size, bubble count, and fluid flow velocity.

18. The method according to claim 13, comprising using the measured additional energy transmitted through the fluid over the measurement time period to determine an independently measured average value of the characteristic of the fluid over the measurement time period.

19. The method according to claim 18, comprising determining a value of a goal function from the estimated average value of the characteristic of the fluid and the independently measured average value of the characteristic of the fluid.

20. The method according to claim 19, wherein the goal function value comprises a difference between the estimated average value of the characteristic of the fluid and the independently measured average value of the characteristic of the fluid.

21. The method according to claim 19, comprising comparing a magnitude of the goal function value with a predetermined threshold value.

22. The method according to claim 21, comprising selectively outputting the estimated temporal variation of the composition of the fluid over the measurement time period according to a result of the comparison between the magnitude of the goal function value and the predetermined threshold value.

23. A method according to claim 21, comprising:
(i) using the measured temporal variation in the property of the electromagnetic field and the calibration data to re-estimate the temporal variation of the composition of the fluid;
(ii) using the re-estimated temporal variation of the composition of the fluid to re-estimate the average value of the characteristic of the fluid over the measurement time period;
(iii) re-determining a value of a goal function from the estimated average value of the characteristic of the fluid and the independently measured average value of the characteristic of the fluid;
(iv) comparing the magnitude of the goal function value with the predetermined threshold value; and
(v) repeating steps (i) to (iv) until the magnitude of the goal function value is less than the predetermined threshold value.

24. A method according to claim 13, wherein the fluid flowing through the fluid flow path comprises at least some liquid during part of the measurement time period and at least some gas during a different part of the measurement time period.

25. The method according to claim 13, wherein the fluid flowing through the fluid flow path comprises a higher proportion of liquid than gas during part of the measurement time period and a higher proportion of gas than liquid during a different part of the measurement time period.

26. The method according to claim 13, wherein the fluid flowing through the fluid flow path is composed substantially of liquid during part of the measurement time period and is composed substantially of gas during a different part of the measurement time period.

27. The method according to claim 13, wherein the composition of the fluid flowing through the fluid flow path alternates between first and second compositions during the measurement time period, and the fluid comprises a higher proportion of liquid than gas in the first composition and the fluid comprises a higher proportion of gas than liquid in the second composition.

28. The method according to claim 27, wherein the fluid is composed substantially of liquid in the first composition and the fluid is composed substantially of gas in the second composition.

29. The method according to claim 27, wherein the composition of the fluid flowing through the fluid flow path alternates periodically between the first and second compositions during the measurement time period.

30. The method according to claim 13, wherein the calibration data comprising values of the property of the electromagnetic field as a function of gas void fraction and liquid composition over a calibration time period.

31. The method according to claim 30, wherein a duration of the calibration time period is equal to a duration of the measurement time period.

32. The method according to claim 13, wherein the fluid comprises water and a further liquid in addition to water.

33. The method according to claim 32, wherein the further liquid comprises oil.

34. The method according to claim 32, wherein the liquid composition comprises, or is expressed as, a water-cut value.

35. The method according to claim 34, wherein the calibration data comprises the property of the electromagnetic field as a function of gas void fraction and water-cut value.

36. The method according to claim 35, wherein the calibration data comprises a plurality of curves, each curve comprising the property of the electromagnetic field as a function of water-cut for a different gas void fraction value.

37. The method according to claim 34, wherein the calibration data comprises a plurality of curves, each curve comprising the property of the electromagnetic field as a function of gas void fraction for a different water-cut value.

38. The method according to claim 13, comprising:
    identifying a recurring feature in the measured temporal variation of the property of the electromagnetic field; and
    determining a nominal value of the property of the electromagnetic field associated with the recurring feature.

39. The method according to claim 38, wherein the recurring feature comprises at least one of a recurring dip, a recurring reduction, and a recurring local minimum.

40. The method according to claim 38, comprising selecting the measurement time period according to the number of instances and/or the nature of the recurring feature.

41. The method according to claim 38, comprising measuring the property of the electromagnetic field repeatedly until the recurring feature is observed a predetermined number of times.

42. The method according to claim 38, comprising estimating a nominal gas void fraction value associated with the recurring feature.

43. The method according to claim 42, comprising estimating the nominal gas void fraction value to be zero.

44. The method according to claim 42, comprising using the nominal value of the property of the electromagnetic field and the nominal gas void fraction value in conjunction with the calibration data to estimate a nominal composition of any liquids flowing through the fluid conduit over the measurement time period.

45. The method according to claim 44, comprising using the nominal liquid composition and the calibration data to translate the measured temporal variation of the property of the electromagnetic field into an estimated temporal variation of gas void fraction over the measurement time period, the nominal liquid composition and the estimated temporal variation of gas void fraction over the measurement time period together constituting an estimated temporal variation of the composition of the fluid over the measurement time period.

46. The method according to claim 45, comprising averaging the estimated temporal variation in the gas void fraction over the measurement time period to determine the estimated average value of the characteristic of the fluid over the measurement time period.

47. The method according to claim 45, comprising using the estimated temporal variation of gas void fraction over the measurement time period and the nominal liquid composition in conjunction with a known value of the property for each fluid component to determine an estimated temporal variation in the property of the fluid over the measurement time period.

48. The method according to claim 45, comprising averaging the estimated temporal variation in the property of the fluid over the measurement time period to determine the estimated average value of the characteristic of the fluid over the measurement time period.

49. The method according to claim 1, wherein the electrically non-conductive material of the wall defines at least part of a thickness of the wall.

50. An apparatus for use in measuring a composition of a multiphase fluid, the apparatus comprising:
    a fluid conduit having a wall defining a fluid flow path for a multiphase fluid, the wall comprising an electrically non-conductive material;
    an electromagnetic measurement arrangement for establishing an electromagnetic field which extends through the electrically non-conductive material of the wall of the fluid conduit into the fluid and for measuring a property of the electromagnetic field over a measurement time period; and
    a fluid measurement arrangement for transmitting additional energy through the fluid over the measurement time period independently of the electromagnetic field and measuring the additional energy transmitted through the fluid over the measurement time period, wherein the electromagnetic field comprises a radio frequency (RF) electromagnetic field, wherein the property of the electromagnetic field comprises a resonant frequency of the electromagnetic field, wherein the electromagnetic measurement arrangement comprises a confinement arrangement for at least partially confining the electromagnetic field, wherein the confinement arrangement is configured to establish the electromagnetic field across the fluid flow path and wherein the confinement arrangement defines a resonant cavity for the electromagnetic field through which the fluid flow path extends, wherein the fluid conduit has a transverse cross-section in a plane transverse to the fluid flow path, which transverse cross-section is symmetrical about one or more lines of symmetry and wherein the fluid measurement arrangement comprises:
    a source of a beam of the additional energy positioned on one side of the fluid conduit; and
    a detector of the beam of the additional energy positioned on the other side of the fluid conduit,
    wherein the source and the detector are arranged relative to the fluid conduit for the transmission of the beam of the additional energy across the fluid conduit from the source to the detector so that the only area in the transverse plane within the wall which is exposed to the beam of the additional energy is generally defined by one of the one or more lines of symmetry and the wall, and wherein the exposed area constitutes between 40% and 60% of a total area defined by the wall in the transverse plane.

51. The apparatus according to claim 50, wherein the additional energy transmitted through the fluid comprises electromagnetic energy of a different frequency to the electromagnetic field.

52. The apparatus according to claim 50, wherein the additional energy transmitted through the fluid comprises at least one of gamma radiation, gamma-rays, X-ray radiation and X-rays.

53. The apparatus according to claim 50, wherein the additional energy transmitted through the fluid is of a different type to any energy coupled between the electromagnetic field and the fluid.

54. The apparatus according to claim 50, wherein the additional energy transmitted through the fluid comprises acoustic energy.

55. The apparatus according to claim 50, wherein the fluid conduit comprises a plurality of sections which are attached together to define the fluid flow path, the electromagnetic field extends through the electrically non-conductive material of the wall of one section into the fluid, and the additional energy is transmitted through fluid flowing through a portion of the fluid flow path defined by a wall of a different section of the fluid conduit.

56. The apparatus according to claim 50, wherein the electrically non-conductive material of the wall defines at least part of a thickness of the wall of the fluid conduit.

57. The apparatus according to claim 50, wherein the wall of the fluid conduit is formed from the electrically non-conductive material.

58. The apparatus according to claim 50, wherein the wall of the fluid conduit comprises or is formed from a polymer material.

59. The apparatus according to claim 50, wherein the wall of the fluid conduit comprises or is formed from a polyether ether ketone (PEEK) material.

60. The apparatus according to claim 50, wherein the resonant cavity includes the electrically non-conductive material of the wall of the fluid conduit.

61. The apparatus according to claim 50, wherein the exposed area constitutes between 45% and 55%, between 49% and 51%, substantially equal to 50%, or 50% of the total area.

62. The apparatus according to claim 50, wherein the source and the detector are arranged relative to the fluid conduit for the transmission of the beam of the additional energy from the source to the detector along a beam axis which is parallel to, but offset from, the one of the one or more lines of symmetry in the transverse plane.

63. The apparatus according to claim 50, wherein the source and the detector are arranged relative to the fluid conduit for the transmission of the beam of the additional energy through the electrically non-conductive material.

\* \* \* \* \*